US006410240B1

(12) United States Patent
Hodge et al.

(10) Patent No.: US 6,410,240 B1
(45) Date of Patent: Jun. 25, 2002

(54) RGS-CONTAINING MOLECULES AND USES THEREOF

(75) Inventors: Martin R. Hodge, Arlington; David Yowe, North Quincy, both of MA (US)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/498,959

(22) Filed: Feb. 4, 2000

Related U.S. Application Data

(63) Continuation-in-part of application No. 09/244,314, filed on Feb. 4, 1999, now Pat. No. 6,274,362.

(51) Int. Cl.$^7$ .......................... C12Q 1/68; G01N 33/53; C07K 14/00; C07H 17/00
(52) U.S. Cl. .......................... 435/6; 435/7.1; 435/325; 435/252.3; 530/350; 530/300; 536/23.1
(58) Field of Search ............................ 435/6, 7.1, 325, 435/252.3; 530/350, 300; 536/23.1

(56) References Cited

PUBLICATIONS

Chatterjee et al. (1997), "Genomic Organization, 5'–Flanking Region, and Chromosomal Localization of the Human RGS3 Gene," *Genomics* 45:429–433, Academic Press, USA.

Popov et al. (1997), "The Regulators of G Protein Signaling (RGS) Domains of RGS4, RGS10, and GAIP Retain GTPase Activating Protein Activity In Vitro," *Proc. Natl. Acad. Sci. USA* 94:7216–7220, National Academy of Sciences, USA.

Snow et al. (1997), "Molecular Cloning and Expression Analysis of Rat Rgs 12 and Rgs14," *Biochemical and Biophysical Research Communications* 233:770–777, Academic Press, USA.

Bowman et al. (1998), "Regulation of Chemotactic and Proadhesive Responses to Chemoattractant Receptors by RGS (Regulator of G–protein Signaling) Family Members," *The Journal of Biological Chemistry* 273(43):28040–28048, USA.

Tseng and Zang (1998), "Role of Regulator of G Protein Signaling in Desensitization of the Glucose–dependent Insulinotropic Peptide Receptor," *Endocrinology* 139(11):4470–4475, The Endocrine Society, USA.

BLASTN Search of h16395 vs. NRN Database.

BLASTN Search of h16395 vs. Dbest Database.

BLASTN Search of h16395 vs. Patent Database.

BLASTN Search of m1975 vs. NRN Database.

BLASTX Search of h16395 vs. NRP Database.

BLASTX Search of m1975 vs. NRP Database.

Swiss–Prot Entry, Accession No. P41220, Siderovski et al. (1994), "A Human Gene Encoding a Putative Basic Helix–Loop–Helix Phosphoprotein Whose mRNA Increases Rapidly in Cycloheximide–treated Blood Mononuclear Cells," *DNA Cell Biol.* 13(2):125–147; Sequence from BLASTX Search of h16395 and m1975.

Swiss–Prot Entry, Accession No. P49798, Druey et al. (1996), "Inhibition of G–protein–mediated MAP Kinase Activation by a New Mammalian Gene Family," *Nature* 379(6567):742–746; Sequence from BLASTX Search of h16395 and m1975.

GenBank Accession No. AAB84001, Chatterjee and Fisher, Direct Submission, Submitted Oct. 1, 1997; Sequence from BLASTX Search of h16395 and m1975.

*Primary Examiner*—Karen Cochrane Carlson
(74) *Attorney, Agent, or Firm*—Millenium Pharmaceuticals, Inc.

(57) ABSTRACT

Novel RGS polypeptides, proteins, and nucleic acid molecules are disclosed. In addition to isolated, full-length RGS proteins, the invention further provides isolated RGS fusion proteins, antigenic peptides, and anti-RGS antibodies. The invention also provides RGS nucleic acid molecules, recombinant expression vectors containing a nucleic acid molecule of the invention, host cells into which the expression vectors have been introduced, and nonhuman transgenic animals in which an RGS gene has been introduced or disrupted. Diagnostic, screening, and therapeutic methods utilizing compositions of the invention are also provided.

50 Claims, 7 Drawing Sheets h16395

1
METTLLFFSQINMCESKEKTFFKLIHGSGKEETSKEAKIRAKEKRNRLSLLVQKPE

FHEDTRSSRSGHLAKETRVSPEEAV<u>KWGESFDKLLSHRDGLEAFTRFLKTEFSEE
N</u>

<u>IEFWIACEDFKKSKGPQQIHLKAKAIYEKFIQTDAPKEVNLDFHTKEVITNSITQPT
L</u>

<u>HSFDAAQSRVYQLMEQDSYTRFLKSDIYLDL</u>MEGRPQRPTNLRRRSRSFTCNEFQ
D
              235
VQSDVAIWL

1
MDMSLVFFSQLNMCESKEKTFFKLMHGSGKEETSIEADIRAKEKRNRLSLLLQRP

DFHGETQASRSALLAKETRVSPEEAV<u>KWAESFDKLLSHRDGVDAFTRFLKTEFSE
E</u>

<u>NIEFWVACEDFKKCKEPQQIILKAKAIYEKFIQNDAPKEVNIDFHTKEVIAKSIAQP
I</u>

<u>LHSFDTAQSRVYQLMEHDSYKRFLKSETYLHL</u>IEGRPQRPTNLRRRSRSFTYNDF
Q
              235
DVKSDVAIWL

FIG. 1B.

```
        10              20              30
 1  METTLFFSQINMCESKEKTFFKLIHGSGK    16395 ORF
 1  MDMSLVFFSQLNMCESKEKTFFKLMHGSGK   1975 ORF 40              50              60
31  EETSKEAKIRAKEKRNRLSLLYQKPEFHED   16395 ORF
31  EETSTEAKIRAKEKRNRLSLLLQRPDFHGE   1975 ORF 70              80              90
61  TRSSRSGHLAKETRVSPEEAVKWGESFDKL   16395 ORF
61  TQASRSAELAKETRVSPEEAVKWAESFDKL   1975 ORF 100             110             120
91  LSHRDGLEAFTRFLKIEFSEENIEFWIACE   16395 ORF
91  LSHRDGVDAFTRFLKIEFSEENIEFWVACE   1975 ORF 130             140             150
121 DFKKSKGPQQIHLKAKAIYEKFIQIDAPKE   16395 ORF
121 DFKKCKEPQQITLKAKAIYEKFIQNDAPKE   1975 ORF 160             170             180
151 VNLDFHIKEVITNSITQPTLHSFDAAQSRV   16395 ORF
151 VNIDFHIKEVIAKSIADPTLHSFDTAQSRV   1975 ORF 190             200             210
181 YQLMEQDSYTRFLKSDIYLDLMEGRPQRPT   16395 ORF
181 YQLMEHDSYKRFLKSETYLHLTEGRPQRPT   1975 ORF 220             230
211 NLRRRSRSFTCNEFQDVQSDVAIWL        16395 ORF
211 NLRRRSRSFTYNDFQDVKSDVAIWL        1975 ORF
```

Decoration 'Decoration #1': Shade (with dots) residues that match the Consensus exactly.

SEQUENCE LISTING

```
<160> NUMBER OF SEQ ID NOS: 12

<210> SEQ ID NO 1
<211> LENGTH: 2217
<212> TYPE: DNA
<213> ORGANISM: Homo sapiens
<220> FEATURE:
<221> NAME/KEY: CDS
<222> LOCATION: (160)...(867)

<400> SEQUENCE: 1
gaattcggct tccatcctaa tacgactcac tatagggctc gagcggccgc ccgggcaggt      60 ataactttt attctactat gtatatgtat ggaatagtat taataaatga actagggaag     120
gatgtaataa attagacatc tcttcatttt agagagaag atg gaa aca aca ttg       174
                                            Met Glu Thr Thr Leu
                                              1               5 ctt ttc ttt tct caa ata aat atg tgt gaa tca aaa gaa aaa act ttt      222
Leu Phe Phe Ser Gln Ile Asn Met Cys Glu Ser Lys Glu Lys Thr Phe
             10                  15                  20 ttc aag tta ata cat ggt tca gga aaa gaa gaa aca agc aaa gaa gcc      270
Phe Lys Leu Ile His Gly Ser Gly Lys Glu Glu Thr Ser Lys Glu Ala
         25                  30                  35 aaa atc aga gct aag gaa aaa aga aat aga cta agt ctt ctt gtg cag      318
Lys Ile Arg Ala Lys Glu Lys Arg Asn Arg Leu Ser Leu Leu Val Gln
     40                  45                  50 aaa cct gag ttt cat gaa gac acc cgc tcc agt aga tct ggg cac ttg      366
Lys Pro Glu Phe His Glu Asp Thr Arg Ser Ser Arg Ser Gly His Leu
 55                  60                  65 gcc aaa gaa aca aga gtc tcc cct gaa gag gca gtg aaa tgg ggt gaa      414
Ala Lys Glu Thr Arg Val Ser Pro Glu Glu Ala Val Lys Trp Gly Glu
 70                  75                  80                  85 tca ttt gac aaa ctg ctt tcc cat aga gat gga cta gag gct ttt acc      462
Ser Phe Asp Lys Leu Leu Ser His Arg Asp Gly Leu Glu Ala Phe Thr
                 90                  95                 100
```

```
aga ttt ctt aaa act gaa ttc agt gaa gaa aat att gaa ttt tgg ata    510
Arg Phe Leu Lys Thr Glu Phe Ser Glu Glu Asn Ile Glu Phe Trp Ile
            105                 110                 115 gcc tgt gaa gat ttc aag aaa agc aag gga cct caa caa att cac ctt    558
Ala Cys Glu Asp Phe Lys Lys Ser Lys Gly Pro Gln Gln Ile His Leu
        120                 125                 130 aaa gca aaa gca ata tat gag aaa ttt ata cag act gat gcc cca aaa    606
Lys Ala Lys Ala Ile Tyr Glu Lys Phe Ile Gln Thr Asp Ala Pro Lys
    135                 140                 145 gag gtt aac ctt gat ttt cac aca aaa gaa gtc att aca aac agc atc    654
Glu Val Asn Leu Asp Phe His Thr Lys Glu Val Ile Thr Asn Ser Ile
150                 155                 160                 165 act caa cct acc ctc cac agt ttt gat gct gca caa agc aga gtg tat    702
Thr Gln Pro Thr Leu His Ser Phe Asp Ala Ala Gln Ser Arg Val Tyr
                170                 175                 180 cag ctc atg gaa caa gac agt tat aca cgt ttt ctg aaa tct gac atc    750
Gln Leu Met Glu Gln Asp Ser Tyr Thr Arg Phe Leu Lys Ser Asp Ile
            185                 190                 195 tat tta gac ttg atg gaa gga aga cct cag aga cca aca aat ctt agg    798
Tyr Leu Asp Leu Met Glu Gly Arg Pro Gln Arg Pro Thr Asn Leu Arg
        200                 205                 210 aga cga tca cgc tca ttt acc tgc aat gaa ttc caa gat gta caa tca    846
Arg Arg Ser Arg Ser Phe Thr Cys Asn Glu Phe Gln Asp Val Gln Ser
    215                 220                 225 gat gtt gcc att tgg tta taa agaaaattga ttttgctcat ttttatgaca       897
Asp Val Ala Ile Trp Leu  *
230                 235 aacttataca tctgcttcta acatatcgca tgtttatgtt aagatttggt cccatccttt   957
aaactgaaat atgtcatgtg aaattatttt aaaaatgtaa aaacaaaact ttctgctaac  1017
aaaatacata cagtatctgc cagtatattc tgtaaaacct tctatttgat gtcattccat  1077
ttataatcag aaaaaaaact tatttcttaa tcaaaggca gtacaaaaaa agtaataatg   1137
ttttataaga ttgtagagtt aagtaaaagt taagcttttg caaagttgtc aaaagttcaa  1197
acaaaagtct agttgggatt ttttaccaaa gcagcataat atgtgttata taaacataat  1257
aatactcaga tatccaaatg ttcagatagc atttttcata atgaatgttc tctttttttt  1317
ggtaatagtg tagaagtgat ctggttctta caatgggaga tgaagaacat ttattattgg  1377
gttactacta accctgtccc aagaatagta atatcacctc tagttataag ccagcaacag  1437 gaactttgt gaagacacat tcatctctac agaacttcag attaaatata atctagatta   1497
atgactgaga ataagatcca catttgaact cattcctaag tgaacatgga cgtacccagt  1557
tatacaaagt acttctgttg gtcacagaaa catgaccaga ttttgcatat ctccaggtag  1617
ggaactaagt agactacctt atcaccggct aagaaaactt gctactaaac tattaggcca  1677
tcaatggctt gaataaaaac cagagaaggt tttcccagg acgtctcatg tttggccctt   1737
tagaattggg gtagaaatca gaatgagat gaggggaaga agcaaggagt ctaaggccct   1797
agcgatttgg gcatctgcca cattggttca tattcagaaa gtgttatctc attgattata  1857
ttcttgttaa gcaaatctcc ttaagtaatt attattcaaa taagattata ctcatacatc  1917
tatatgtcac tgttttaaag agatatttaa tttttaatgt gtgttacatg gtctgtaaat  1977
atttgtattt aaaaatgcca tgcattaggc tttggaaatt taatgttagt tgaaatgtaa  2037
aatgtgaaaa cttagatca tttgtagtaa taaatatttt taacttcatt catacagtta   2097
agtttatctg acaataaaag ctctgactga atgttgatta tccttcctat tatgtaataa  2157
```

```
ggaataaaca ttttcttctt ttagagtaaa aaaaaaaaaa aaaaaaaaaa gggcggccgc    2217
```

<210> SEQ ID NO 2
<211> LENGTH: 235
<212> TYPE: PRT
<213> ORGANISM: Homo sapiens

<400> SEQUENCE: 2

```
Met Glu Thr Thr Leu Leu Phe Phe Ser Gln Ile Asn Met Cys Glu Ser
 1               5                  10                  15

Lys Glu Lys Thr Phe Phe Lys Leu Ile His Gly Ser Gly Lys Glu Glu
             20                  25                  30

Thr Ser Lys Glu Ala Lys Ile Arg Ala Lys Glu Lys Arg Asn Arg Leu
         35                  40                  45

Ser Leu Leu Val Gln Lys Pro Glu Phe His Glu Asp Thr Arg Ser Ser
 50                  55                  60

Arg Ser Gly His Leu Ala Lys Glu Thr Arg Val Ser Pro Glu Glu Ala
 65                  70                  75                  80

Val Lys Trp Gly Glu Ser Phe Asp Lys Leu Leu Ser His Arg Asp Gly
                 85                  90                  95

Leu Glu Ala Phe Thr Arg Phe Leu Lys Thr Glu Phe Ser Glu Glu Asn
            100                 105                 110

Ile Glu Phe Trp Ile Ala Cys Glu Asp Phe Lys Lys Ser Lys Gly Pro
        115                 120                 125

Gln Gln Ile His Leu Lys Ala Lys Ala Ile Tyr Glu Lys Phe Ile Gln
    130                 135                 140

Thr Asp Ala Pro Lys Glu Val Asn Leu Asp Phe His Thr Lys Glu Val
145                 150                 155                 160

Ile Thr Asn Ser Ile Thr Gln Pro Thr Leu His Ser Phe Asp Ala Ala
                165                 170                 175

Gln Ser Arg Val Tyr Gln Leu Met Glu Gln Asp Ser Tyr Thr Arg Phe
            180                 185                 190

Leu Lys Ser Asp Ile Tyr Leu Asp Leu Met Glu Gly Arg Pro Gln Arg
        195                 200                 205

Pro Thr Asn Leu Arg Arg Arg Ser Arg Ser Phe Thr Cys Asn Glu Phe
    210                 215                 220

Gln Asp Val Gln Ser Asp Val Ala Ile Trp Leu
225                 230                 235
```

<210> SEQ ID NO 3
<211> LENGTH: 1164
<212> TYPE: DNA
<213> ORGANISM: Mus sp.
<220> FEATURE:
<221> NAME/KEY: CDS
<222> LOCATION: (134)...(841)

<400> SEQUENCE: 3

```
tttttgtaag aaaaatctga ggaaagattc gggatagcgc tttattcagg atgttttcct      60
atgaaatagc attcatctgt gggagagaga aggactaagg aaatctgaca tctgttggtc     120
actgggacag aat atg gat atg tca ctg gtt ttc ttc tct caa tta aat       169
               Met Asp Met Ser Leu Val Phe Phe Ser Gln Leu Asn
                1               5                  10 atg tgt gaa tca aaa gag aaa act ttt ttc aaa cta atg cat ggg tca      217
Met Cys Glu Ser Lys Glu Lys Thr Phe Phe Lys Leu Met His Gly Ser
         15                  20                  25 ggg aaa gaa gaa aca agc atc gag gcc aaa atc aga gcg aaa gaa aaa     265
```

```
Gly Lys Glu Glu Thr Ser Ile Glu Ala Lys Ile Arg Ala Lys Glu Lys
         30                  35                  40 agg aat aga cta agt ctt ctc cta cag agg cct gac ttc cat gga gag    313
Arg Asn Arg Leu Ser Leu Leu Leu Gln Arg Pro Asp Phe His Gly Glu
 45                  50                  55                  60 act caa gcc agt aga tct gcc ctc ttg gcc aaa gaa aca aga gtc tct    361
Thr Gln Ala Ser Arg Ser Ala Leu Leu Ala Lys Glu Thr Arg Val Ser
                 65                  70                  75 cct gaa gaa gca gtg aaa tgg gct gaa tca ttt gac aaa ttg ctc tct    409
Pro Glu Glu Ala Val Lys Trp Ala Glu Ser Phe Asp Lys Leu Leu Ser
                     80                  85                  90 cat aga gat gga gtg gat gct ttt acc aga ttt ctt aaa act gaa ttc    457
His Arg Asp Gly Val Asp Ala Phe Thr Arg Phe Leu Lys Thr Glu Phe
                         95                 100                 105 agt gag gag aac att gaa ttt tgg gtc gcc tgt gaa gac ttc aag aaa    505
Ser Glu Glu Asn Ile Glu Phe Trp Val Ala Cys Glu Asp Phe Lys Lys
        110                 115                 120 tgc aag gaa cct caa caa atc atc cta aaa gca aag gca atc tat gag    553
Cys Lys Glu Pro Gln Gln Ile Ile Leu Lys Ala Lys Ala Ile Tyr Glu
125                 130                 135                 140 aaa ttc att cag aat gat gcc ccc aaa gag gtt aac att gat ttt cat    601
Lys Phe Ile Gln Asn Asp Ala Pro Lys Glu Val Asn Ile Asp Phe His
                    145                 150                 155 act aaa gaa gta att gct aag agc atc gcc cag ccc act ctc cac agt    649
Thr Lys Glu Val Ile Ala Lys Ser Ile Ala Gln Pro Thr Leu His Ser
                        160                 165                 170 ttt gat acg gca caa agc aga gtg tac cag ctc atg gaa cat gac agt    697
Phe Asp Thr Ala Gln Ser Arg Val Tyr Gln Leu Met Glu His Asp Ser
                            175                 180                 185 tat aaa cgc ttt ttg aaa tct gag acc tac tta cat ttg ata gaa gga    745
Tyr Lys Arg Phe Leu Lys Ser Glu Thr Tyr Leu His Leu Ile Glu Gly
        190                 195                 200 aga cct cag aga cca aca aac ctt agg aga cga tca cga tca ttt act    793
Arg Pro Gln Arg Pro Thr Asn Leu Arg Arg Arg Ser Arg Ser Phe Thr
205                 210                 215                 220 tac aat gat ttc caa gat gta aag tca gat gtt gcc att tgg tta tga    841
Tyr Asn Asp Phe Gln Asp Val Lys Ser Asp Val Ala Ile Trp Leu
                    225                 230                 235 gtaaaagtca tttgtcttct tttgatagtg tatgtgtata tctaaaatat atactaatac    901
taatgtgtac ttctaaaata tagcttgtgt ataagaagag atgatttcat ttttaaaata    961
caccatgcaa atacatatta aatgtaagaa cttttttatat tatactaaaa taattcatca   1021
tctatcttcc gaaatatttt atgaaaatct atctgatatt ctattctaat aaaattcttt   1081
atttctacaa taacagtcag taagaagaag ctttgaagcc gaattccagc acactggcgg   1141
ccggtactag tggatccgag ctc                                            1164

<210> SEQ ID NO 4
<211> LENGTH: 235
<212> TYPE: PRT
<213> ORGANISM: Mus sp.

<400> SEQUENCE: 4

Met Asp Met Ser Leu Val Phe Phe Ser Gln Leu Asn Met Cys Glu Ser
 1               5                  10                  15

Lys Glu Lys Thr Phe Phe Lys Leu Met His Gly Ser Gly Lys Glu Glu
                 20                  25                  30

Thr Ser Ile Glu Ala Lys Ile Arg Ala Lys Glu Lys Arg Asn Arg Leu
             35                  40                  45
```

Ser Leu Leu Gln Arg Pro Asp Phe His Gly Glu Thr Gln Ala Ser
    50                  55                  60

Arg Ser Ala Leu Leu Ala Lys Glu Thr Arg Val Ser Pro Glu Ala
65                  70                  75                  80

Val Lys Trp Ala Glu Ser Phe Asp Lys Leu Leu Ser His Arg Asp Gly
                85                  90                  95

Val Asp Ala Phe Thr Arg Phe Leu Lys Thr Glu Phe Ser Glu Glu Asn
                100                 105                 110

Ile Glu Phe Trp Val Ala Cys Glu Asp Phe Lys Lys Cys Lys Glu Pro
                115                 120                 125

Gln Gln Ile Ile Leu Lys Ala Lys Ala Ile Tyr Glu Lys Phe Ile Gln
    130                 135                 140

Asn Asp Ala Pro Lys Glu Val Asn Ile Asp Phe His Thr Lys Glu Val
145                 150                 155                 160

Ile Ala Lys Ser Ile Ala Gln Pro Thr Leu His Ser Phe Asp Thr Ala
                165                 170                 175

Gln Ser Arg Val Tyr Gln Leu Met Glu His Asp Ser Tyr Lys Arg Phe
                180                 185                 190

Leu Lys Ser Glu Thr Tyr Leu His Leu Ile Glu Gly Arg Pro Gln Arg
                195                 200                 205

Pro Thr Asn Leu Arg Arg Arg Ser Arg Ser Phe Thr Tyr Asn Asp Phe
    210                 215                 220

Gln Asp Val Lys Ser Asp Val Ala Ile Trp Leu
225                 230                 235

<210> SEQ ID NO 5
<211> LENGTH: 42
<212> TYPE: DNA
<213> ORGANISM: Homo sapiens

<400> SEQUENCE: 5
agtccgggat ccaaaaaaat ggaaacaaca ttgctttct tt          42

<210> SEQ ID NO 6
<211> LENGTH: 39
<212> TYPE: DNA
<213> ORGANISM: Homo sapiens

<400> SEQUENCE: 6
ccgtacgtcg acttataacc aaatggcaac atctgattg             39

<210> SEQ ID NO 7
<211> LENGTH: 27
<212> TYPE: DNA
<213> ORGANISM: Homo sapiens

<400> SEQUENCE: 7
tgactgagaa taagatccac atttgaa                          27

<210> SEQ ID NO 8
<211> LENGTH: 27
<212> TYPE: DNA
<213> ORGANISM: Homo sapiens

<400> SEQUENCE: 8
catgtttctg tgaccaacag aagtact                          27

<210> SEQ ID NO 9

```
<211> LENGTH: 32
<212> TYPE: DNA
<213> ORGANISM: Homo sapiens

<400> SEQUENCE: 9
tcattcctaa gtgaacatgg acgtacccag tt                                    32

<210> SEQ ID NO 10
<211> LENGTH: 21
<212> TYPE: DNA
<213> ORGANISM: Homo sapiens

<400> SEQUENCE: 10
cacccccact gaaaaagatg a                                                21

<210> SEQ ID NO 11
<211> LENGTH: 26
<212> TYPE: DNA
<213> ORGANISM: Homo sapiens

<400> SEQUENCE: 11
cttaactatc ttgggctgtg acaaag                                           26

<210> SEQ ID NO 12
<211> LENGTH: 24
<212> TYPE: DNA
<213> ORGANISM: Homo sapiens

<400> SEQUENCE: 12
tatgcctgcc gtgtgaacca cgtg                                             24
```

RGS-CONTAINING MOLECULES AND USES THEREOF

CROSS-REFERENCE TO RELATED APPLICATION

This application is a Continuation-in-Part of U.S. application Ser. No. 09/244,314, filed Feb. 4, 1999, now U.S. Pat. No. 6,274,362 entitled "Novel RGS-Containing Molecules and Uses Thereof". The contents of this copending application are incorporated herein by reference.

FIELD OF THE INVENTION

The invention relates to novel RGS (regulators of G-protein signaling) nucleic acids and proteins. Also provided are vectors, host cells, and recombinant methods for making and using the novel molecules.

BACKGROUND OF THE INVENTION

Regulators of G-protein signaling (RGS) accelerate guanosine triphosphate (GTP) hydrolysis by $G_i$, but not by $G_s$ class $\alpha$-subunits (Popov et al. (1997) *Proc. Natl. Acad. Sci. USA* 94:7216–20). RGS proteins were first identified in genetic screens in fungi and nematodes as negative regulators of G-protein signaling (Dolhman et al. (1995) *Mol. Cell. Biol.* 15:3635–43). RGS proteins have been shown to function as GTPase-activating proteins. It has additionally been proposed that RGS proteins may act as effector antagonists by occluding the effector-binding sites on G-protein $\alpha$-subunits (Helper et al. (1997) *Proc. Natl. Acad. Sci. USA* 94:428–432).

RGS has been implicated in a distinct molecular mechanism with the potential to modulate G-protein responses. Proteins containing the RGS domain can directly control aspects of G-protein stimulated signaling pathways. RGS proteins appear to enhance the endogenous GTPase activity of G-proteins, thus decreasing the half-life of the active GTP-bound state and limiting the duration of $G_{\alpha i}$ signaling.

The glucose-dependent insulinotropic peptide receptor (GIP-R) is a member of the G-protein coupled receptors. GIP was first isolated from porcine small intestine and was described as a member of the secretin family of gastrointestinal regulatory peptides (Tseng and Zhang (1998) *Endocrin.* 139:4470–75). In the presence of glucose, GIP is a potent stimulator of insulin release by pancreatic islet β-cells. GIP may represent an important hormonal mediator in the entero-insular axis. Insulinotropic properties of GIP in diabetic patients have been shown to be diminished despite elevated serum levels of GIP. While the precise mechanism for the decline in insulinotropic activity of GIP in diabetic patients has not been defined, agonist-induced desensitization of G-protein-coupled receptors is well documented (Premont et al. (1995) *FASEB J* 9:175–182).

Recently, an interaction of the G-protein with members of RGS proteins has been demonstrated to mediate a desensitization mechanism. RGS proteins act as GTPase activating proteins to decrease the half-life of the activated G $_{\alpha}$-subunit (Koelle et al. (1996) *Cell* 84:115–125; Druey et al. (1996) *Nature* 379:742–46).

Additionally, RGS proteins may be involved in cell migration. Cell migration is a required behavior in the development and maintenance of multicellular organisms. Generally, cells migrate in response to various chemoattractants and chemorepellents in the environment (Bowman et al. (1998) *J Biol. Chem.* 273:28040–48). Chemoattractants provide a directional signal to cells leading to migration of the cells towards the source of the chemoattractant (Butcher et al. (1996) *Science* 272:60–66; Mackay, C. R. (1996) *J. Exp. Med.* 184:799–802). Chemoattractants also direct the rapid, integrin-dependent adhesion of leukocytes to various cell-associated or extracellular proteins if the corresponding chemoattractant receptor is expressed at high levels. RGS proteins appear to be involved as most leukocyte chemoattractants mediate their activity by binding and stimulating specific $G_{\alpha i}$-coupled receptors.

RGS proteins constitute a family of proteins characterized by an RGS domain. A number of RGS proteins have been identified and several have been shown to function as GTPase-activating proteins (Chatterjee et al. (1997) *Genomics* 45:429–33). Identification of other members of the RGS family are needed.

Because of the complexity of the immune response and regulation of heterotrimeric G-protein signaling, additional mechanisms are needed to modulate such functions. Additionally, methods are needed to regulate an immune response, and provide therapies for a range of diseases.

SUMMARY OF THE INVENTION

Isolated nucleic acid molecules corresponding to regulators of G-protein signaling (RGS) nucleic acid sequences are provided. Additionally amino acid sequences corresponding to the polynucleotides are encompassed. In particular, the present invention provides for isolated nucleic acid molecules comprising nucleotide sequences encoding the amino acid sequences shown in SEQ ID NOs:2 and 4 or the nucleotide sequences encoding the DNA sequence deposited in a bacterial host as ATCC Accession Number 207048, or the DNA sequence obtained from the overlapping clones deposited as ATCC Accession Numbers 207049 and 207050. By "DNA sequence obtained from the overlapping clones" is intended that the DNA sequence of the human sequence can be obtained by sequencing of the two individual clones which together comprise the entire human sequence. Further provided are RGS polypeptides having an amino acid sequence encoded by a nucleic acid molecule described herein.

The present invention also provides vectors and host cells for recombinant expression of the nucleic acid molecules described herein, as well as methods of making such vectors and host cells and for using them for production of the polypeptides or peptides of the invention by recombinant techniques.

The RGS molecules of the present invention are useful for modulating the phenotype of immune and respiratory responses, particularly for regulating an immune response. The molecules are useful for the diagnosis and treatment of immune and respiratory disorders, including, but not limited to, atopic conditions, such as asthma and allergy, including allergic rhinitis, psoriasis, the effects of pathogen infection, chronic inflammatory diseases, organ-specific autoimmunity, graft rejection, and graft versus host disease. The molecules are also useful for the diagnosis and treatment of hematological disorders, including, but not limited to, disorders associated with an abnormal development, function, or number of blood cells, including, but not limited to, thrombocytopenia or thrombocytosis, granulocytopenia or granulocytosis (e.g., neutropenia or neutrophilia, eosinopenia or eosinophilia, or basophilia), and anemia or polycythemia. Accordingly, in one aspect, this invention provides isolated nucleic acid molecules encoding RGS proteins or biologically active portions thereof, as well as nucleic acid fragments suitable as primers or hybridization probes for the detection of RGS-encoding nucleic acids.

Another aspect of this invention features isolated or recombinant RGS proteins and polypeptides. Preferred RGS proteins and polypeptides possess at least one biological activity possessed by naturally occurring RGS proteins.

Variant nucleic acid molecules and polypeptides substantially homologous to the nucleotide and amino acid sequences set forth in the sequence listings are encompassed by the present invention. Additionally, fragments and substantially homologous fragments of the nucleotide and amino acid sequences are provided.

Antibodies and antibody fragments that selectively bind the RGS polypeptides and fragments are provided. Such antibodies are useful in detecting the RGS polypeptides as well as in regulating G-protein signaling.

In another aspect, the present invention provides a method for detecting the presence of RGS activity or expression in a biological sample by contacting the biological sample with an agent capable of detecting an indicator of RGS activity such that the presence of RGS activity is detected in the biological sample.

In yet another aspect, the invention provides a method for modulating RGS activity comprising contacting a cell with an agent that modulates (inhibits or stimulates) RGS activity or expression such that RGS activity or expression in the cell is modulated. In one embodiment, the agent is an antibody that specifically binds to RGS protein. In another embodiment, the agent modulates expression of RGS protein by modulating transcription of an RGS gene, splicing of an RGS mRNA, or translation of an RGS mRNA. In yet another embodiment, the agent is a nucleic acid molecule having a nucleotide sequence that is antisense to the coding strand of the RGS mRNA or the RGS gene.

In one embodiment, the methods of the present invention are used to treat a subject having a disorder characterized by aberrant RGS protein activity or nucleic acid expression by administering an agent that is an RGS modulator to the subject. In one embodiment, the RGS modulator is an RGS protein. In another embodiment, the RGS modulator is an RGS nucleic acid molecule. In other embodiments, the RGS modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding an RGS protein; (2) misregulation of a gene encoding an RGS protein; and (3) aberrant post-translational modification of an RGS protein, wherein a wild-type form of the gene encodes a protein with an RGS activity.

In another aspect, the invention provides a method for identifying a compound that binds to or modulates the activity of an RGS protein. In general, such methods entail measuring a biological activity of an RGS protein in the presence and absence of a test compound and identifying those compounds that alter the activity of the RGS protein.

The invention also features methods for identifying a compound that modulates the expression of RGS genes by measuring the expression of the RGS sequences in the presence and absence of the compound.

Other features and advantages of the invention will be apparent from the following detailed description and claims.

BRIEF DESCRIPTION OF THE DRAWINGS

FIG. 1 provides the amino sequences for the h16395 and m1975 proteins. FIG. 1A and B provide the human and murine sequences, respectively; the RGS domain is underlined. FIG. 1C provides the alignment of the human sequence with the murine orthologue.

FIG. 2 shows the amino acid sequence alignment for the proteins encoded by h16395 with human RGS2, RGS4, and RGS5. The RGS proteins share closest homology to human RGS5 protein (about 44% sequence identity for the human sequence) as compared to 38% and 39% for RGS2 and RGS4, respectively. The sequence identity was determined by the Clustal method. The region of homology is observed for the RGS domains, amino acids 82–201, with little homology observed for the N-terminal, 1–81, and C-terminal, 202–235, amino acids.

DETAILED DESCRIPTION OF THE INVENTION

Figure 3:
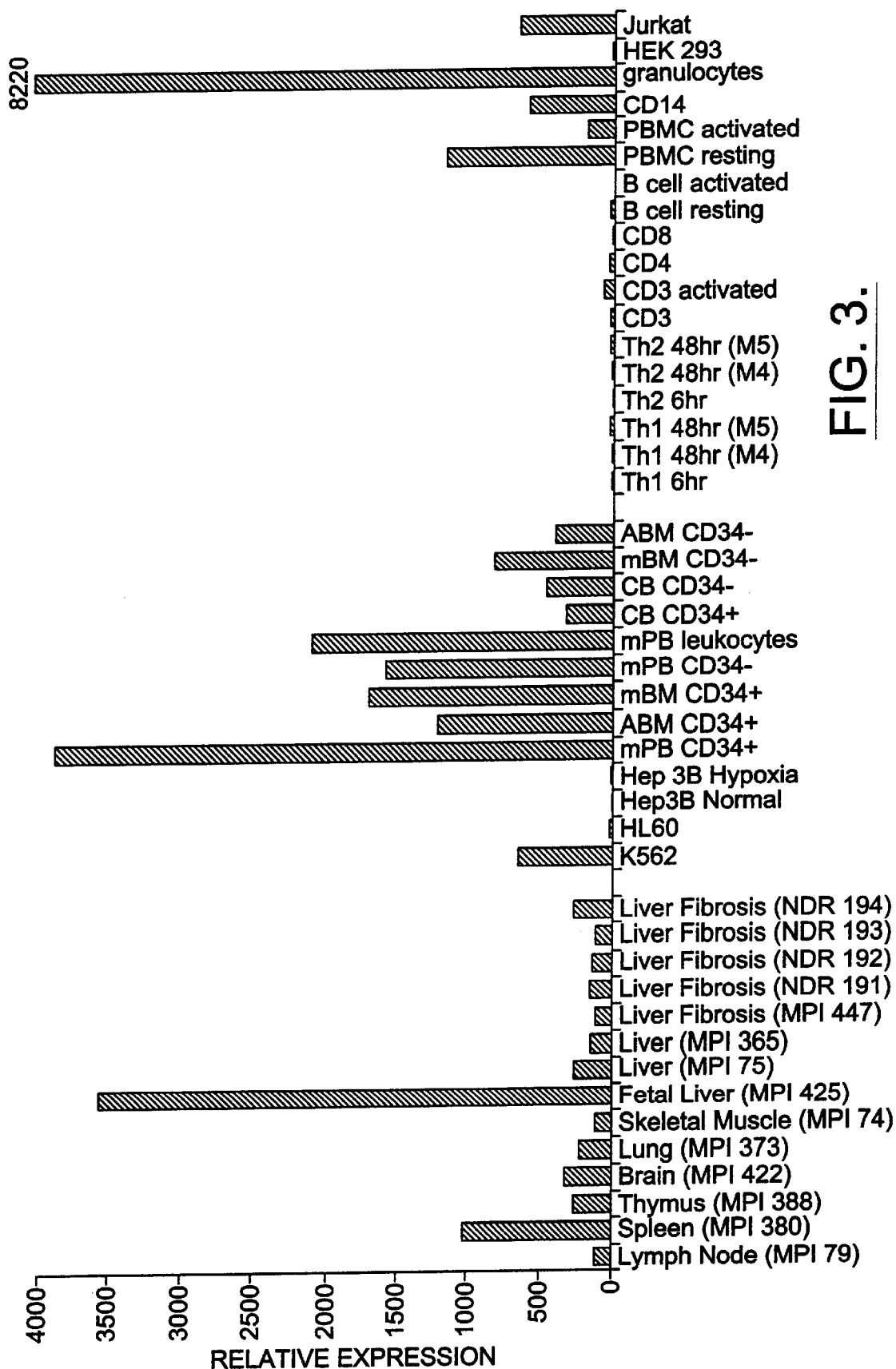
FIG. 3 shows expression of h16395 in a broad panel of normal tissues and cell lines relative to anti-CD3 antibody-stimulated Th1 cells and is described further in Example 4.

The present invention provides isolated nucleic acid molecules comprising a nucleotide sequence encoding the RGS polypeptides whose amino acid sequence is given in SEQ ID NO:2 or 4 respectively, or a variant or fragment of the polypeptide. Nucleotide sequences encoding the RGS proteins of the invention are set forth in SEQ ID NOs:1 and 3.

The present invention relates to methods and compositions for the modulation, diagnosis, and treatment of immune and respiratory disorders, especially RGS related disorders. Such immune disorders include, but are not limited to, chronic inflammatory diseases and disorders, such as Crohn's disease, reactive arthritis, including Lyme disease, insulin-dependent diabetes, organ-specific autoimmunity, including multiple sclerosis, rheumatoid arthritis, inflammatory bowel disease, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

Respiratory disorders include, but are not limited to, apnea, asthma, particularly bronchial asthma, berillium disease, bronchiectasis, bronchitis, bronchopneumonia, cystic fibrosis, diphtheria, dyspnea, emphysema, chronic obstructive pulmonary disease, allergic bronchopulmonary aspergillosis, pneumonia, acute pulmonary edema, pertussis, pharyngitis, atelectasis, Wegener's granulomatosis, Legionnaires disease, pleurisy, rheumatic fever, and sinusitis.

Hematological disorders include, but are not limited to, disorders associated with abnormal differentiation or hematopoiesis, morphology, migration, proliferation, or function of blood cells derived, for example, from myeloid multipotential cells in bone marrow, such as megakaryocytes (and ultimately platelets), monocytes (and tissue macrophages), erythrocytes, and granulocytes (e.g., neutrophils, eosinophils, and basophils) and from lymphoid multipotential cells, such as T and B lymphocytes.

Platelet-associated disorders include, but are not limited to, thrombocytopenia due to a reduced number of megakaryocytes in the bone marrow, for example, as a result of chemotherapy; invasive disorders, such as leukemia, idiopathic or drug- or toxin-induced aplasia of the marrow, or rare hereditary amegakaryocytic thrombocytopenias; ineffective thrombopoiesis, for example, as a result of megaloblastic anemia, alcohol toxicity, vitamin B12 or folate deficiency, myelodysplastic disorders, or rare hereditary disorders (e.g., Wiskott-Aldrich syndrome and May-hegglin anomaly); a reduction in platelet distribution, for example, as a result of cirrhosis, a splenic invasive disease (e.g., Gaucher's disease), or myelofibrosis with extramedullary myeloid metaplasia; increased platelet destruction, for example, as a result of removal of IgG-coated platelets by the mononuclear phagocytic system (e.g., idiopathic thrombocytopenic purpura (ITP), secondary immune thrombocytopenia (e.g., systemic lupus erythematosus, lymphoma, or chronic lymphocytic leukemia), drug-related immune thrombocytopenias (e.g., as with quinidine, aspirin, and heparin), post-transfusion purpura, and neonatal thrombocytopenia as a result of maternal platelet autoantibodies or maternal platelet alloantibodies). Also included are thrombocytopenia secondary to intravascular clotting and thrombin-induced damage to platelets as a result of, for example, obstetric complications, metastatic tumors, severe gram-negative bacteremia, thrombotic thrombocytopenic purpura, or severe illness. Also included is dilutional thrombocytopenia, for example, due to massive hemorrhage.

Platelet-associated disorders also include, but are not limited to, essential thrombocytosis and thrombocytosis associated with, for example, splenectomy, acute or chronic inflammatory diseases, hemolytic anemia, carcinoma, Hodgkin's disease, lymphoproliferative disorders, and malignant lymphomas.

Erythrocyte-associated disorders include anemias such as, for example, hemolytic anemias due to hereditary cell membrane abnormalities, such as hereditary spherocytosis, hereditary elliptocytosis, and hereditary pyropoikilocytosis; hemolytic anemias due to acquired cell membrane defects, such as paroxysmal nocturnal hemoglobinuria and spur cell anemia; hemolytic anemias caused by antibody reactions, for example to the RBC antigens, or antigens of the ABO system, Lewis system, Ii system, Rh system, Kidd system, Duffy system, and Kell system; methemoglobinemia; a failure of erythropoiesis, for example, as a result of aplastic anemia, pure red cell aplasia, myelodysplastic syndromes, sideroblastic anemias, and congenital dyserythropoietic anemia; secondary anemia in nonhematolic disorders, for example, as a result of chemotherapy, alcoholism, or liver disease; anemia of chronic disease, such as chronic renal failure; and endocrine deficiency diseases.

Other erythrocyte-associated disorders include polycythemias such as, for example, polycythemia vera, secondary polycythemia, and relative polycythemia. Neutrophil-associated disorders include neutropenias that result from or accompany a number of conditions, including, but not limited to, chemotherapy; chronic idopathic neutropenia; Felty's syndrome' acute infectious disease, lymphoma or aleukemic lymphocytic leukemia, myelodysplastic syndrome, and rhematic diseases such as systemic lupus erythematosus, rheumatoid arthritis, and polymyositis. Also included is neutrophilia, for example, accompanying chronic myelogenous leukemia.

Other hematological disorders include disorders associated with abnormal monocyte and/or macrophage function, such as impaired phagocytosis, chemotaxis, or secretion of cytokines, growth factors and acute-phase reactants, resulting from certain diseases, e.g., lysosomal storage diseases (e.g., Gaucher's disease); impaired monocyte cytokine production, for example, found in some patients with disseminated nontuberculous mycobacterial infection who are not infected with HIV; leukocyte adhesion deficiency (LAD), hyperimmunoglobulin E-recurrent infection (HIE) or Job's syndrome, Chédiak-Higashi syndrome (CHS), and chronic granulomatous diseases (CGD), certain autoimmune diseases, such as systemic lupus erythematosus and other autoimmune diseases characterized by tissue deposition of immune complexes, as seen in Sjögren's syndrome, mixed cryoglobulinemia, dermatitis herpetiformis, and chronic progressive multiple sclerosis. Also included are disorders or infections that impair mononuclear phagocyte function, for example, influenza virus infection and AIDS.

Monocyte-associated disorders include monocytoses such as, for example, monocytoses associated with certain infections such as tuberculosis, brucellosis, subacute bacterial endocarditis, Rocky Mountain spotted fever, malaria, and visceral leishmaniasis (kala azar), in malignancies, leukemias, myeloproliferative syndromes, hemolytic anemias, chronic idiopathic neutropenias, and granulomatous diseases such as sarcoidosis, regional enteritis, and some collagen vascular diseases.

Other monocyte-associated disorders include monocytopenias such as, for example, monocytopenias that can occur with acute infections, with stress, following administration of glucocorticoids, aplastic anemia, hairy cell leukemia, and acute myelogenous leukemia and as a direct result of administration of myelotoxic and immunosuppressive drugs.

Eosinophil-associated disorders include eosinphilias such as, for example, eosinophilias that result from or accompany conditions such as allergic disorders, infections caused by parasites and other organisms, dermatologic diseases, pulmonary diseases, collagen vascular disease, neoplasms, immunodeficiency diseases, gastroenteritis, inflammatory bowel disease, chronic active hepatitis, pancreatitis, and hypopituitarism. Also included are hypereosinophilic syndrome (HES) and chronic and acute eosinophilic leukemias.

Other eosinophil-associated disorders include eosinopenias such as, for example, eosinopenias that occur with stress, such as acute bacterial infection, and following administration of glucocorticoids.

Basophil-associated disorders include basophilias such as, for example, basophilias seen in myeloproliferative disorders (e.g., chronic myeloid leukemia, polycythemia vera, and myeloid metaplasia), following splenectomy, hemolytic anemia, ulcerative colitis, varicella infection, and Hodgkin's disease.

Two novel genes, human clone h16395 and its corresponding murine orthologue m1975, that are differentially expressed in spleen and in various cells of hematopoietic origin are provided. A Northern blot analysis of h16395 revealed expression in the following tissues in order of highest to lowest expression: peripheral blood leukocytes, spleen, liver, colon, placenta, and heart. Expression of m1975 was greater in the spleen followed by the heart. The sequences were detected in T-cells, monocytes, and granulocytes by RT-PCR. 3'UTR probes were used to avoid cross-hybridization with other RGS proteins. Such sequences are referred to as "RGS" indicating that the genes encode an RGS protein comprising an RGS domain.

The sequences of the invention find use in modulating an immune response as well as other cellular activities. By "modulating" is intended the upregulating or downregulating of a response, particularly a G-protein-mediated signaling response.

The proteins in the RGS-containing protein family act to inhibit G-protein-mediated signaling at the level of the receptor/G-protein interaction or the G-protein $\alpha$ subunit. $G_{\alpha i}$-linked receptors support rapid adhesion and directed migration of leukocytes and other cell types. RGS proteins regulate $G_{\alpha i}$-stimulated pathways. Thus, the compositions of the invention (proteins, polynucleotides, fragments and variants thereof, as well as agonists and antagonists) can be used to modulate cell adhesion and chemotaxis. Movement of fibroblasts into areas of injury plays an important role in wound repair. Further, the migration of endothelial cells performs a paramount role during angiogenesis. Leukocytes are recruited to sites of inflammation, and lymphocytes are recruited to lymphatic organs to promote an immune response. Chemoattractants mediate their activity by binding and stimulating specific $G_{\alpha i}$-coupled receptors. RGS proteins enhance the endogenous GTPase activity of G-proteins, decreasing the half-life of the active GTP-bound state and limiting the duration of $G_{\alpha i}$ signaling. Thus, RGS compositions of the invention can be used to modulate (stimulate or inhibit) cellular migratory and proadhesive responses to chemoattractants. Thus, nucleic acid molecules or antisense nucleic acid molecules of the invention may find use in suppressing or enhancing an immune and/or inflammatory response. Proteins and/or antibodies of the invention are also useful in modulating an immune and/or inflammatory response.

The relatively high levels of h16395 in lymphoid and myeloid tissues and cells derived from these organs is consistent with a role for this RGS in immune cell function. Hence, h16395 may play a role in regulating the cellular response to chemoattractant stimulation, and in doing so effect the deactivation or activation of several intracellular pathways. This is because the majority of chemokine receptors couple through $G_{\alpha i}$ and occasionally $G_{\alpha q}$, both targets of RGS proteins. RGSs accelerate the slow intrinsic GTPase activity of the $G_\alpha$ subunit of heterotrimeric G proteins. This leads to the deactivation of the G-protein coupled receptor (GPCR) signaling pathway due to reassociation of the $G_\alpha$ and $G_{\beta\gamma}$ subunits, preventing their ability to interact with downstream effector molecules. While the invention is not bound by any mechanism of action, RGSs may activate the GPCR signaling pathway by increasing the cycling rate from the active $G_\alpha$ and $G_{\beta\gamma}$ states to the inactive heterotrimeric subunit state, thereby increasing the level of G-protein substrate for activation by the GPCR after ligand interaction.

The importance of chemokine receptors in a wide range of biological processes is reflected by their expression on both leukocyte and non-leukocyte cells. Hence, RGSs h16395/m1975 may be useful in modulating both immune and non-immune cell function, particularly, in the deactivation and/or activation of intracellular pathways, resulting in the directed chemotaxis, adhesion, localization, and prevention of cells to respond to further chemoattractant stimulation. Non-inflammatory (e.g., cell migration during development) or inflammatory stimuli are likely to be responsible for this leukocyte migration. The "hallmark" of inflammation is the infiltration of specific leukocyte subsets from the blood into affected tissues. A variety of chemoattractants (chemokines and classical chemoattractants including formyl peptides, C5a, leukotriene B4 and the like) and their receptors control the directed migration of leukocytes to inflammatory sites. Most of these chemoattractants mediate their activity by GPCR stimulation of inflammatory migrating cells through heterotrimeric G-protein-dependent or -independent pathways. Chemokines can also regulate recruitment of T-lymphocytes in non-inflammatory situations, e.g., lymphocytes must move through tissue compartments during their development and differentiation. Chemokine receptors also play a role in the expression of adhesion molecules during the chemotactic response. Intracellular pathways that have been implicated with chemokine receptor signaling during these cellular responses include calcium mobilization, kinase activation, tyrosine phosphorylation, low molecular weight G-protein regulation, and STAT/JAK activation.

h16395/m1975 are likely to be important in the regulation of chemokine receptor signaling during T-lymphocyte activation and differentiation, depending on their expression pattern and receptor specificity. The precise pattern of chemokine receptor expression depends on the T-cell activation state. In resting T-cells, the chemokine receptor CXCR4 is only expressed. In Th1 and Th2 cells, the chemokine receptors CXCR4, CCR1, and CCR2 are expressed. Several chemokine receptors are also specifically expressed in Th1 versus Th2 cells including CXCR3 and CCR5 in the former and CCR3, CCR4, and CCR7 in the latter.

Based on high expression levels, h16395/m1975 are also likely to be important in the regulation of chemokine receptor signaling during differentiation of megakaryocyte progenitors and maturation of megakaryocytes. The intracellular pathways that h16395 can modulate include the pathway mediated by CXCR4 activation and thromboxane receptors, as well as cytokine receptors, such as c-Mpl.

The low expression levels of h16395 in post-mitotic tissues, and the relatively high levels in the more mitotic tissues is consistent with a role for this RGS in cell proliferation. GPCRs are known to be expressed in proliferating cells, and many ligands acting via these receptors are known to elicit a mitogenic response. Furthermore, overexpression of the p53-responsive gene A28-RGS14 inhibits both $G_i$ and $G_q$ coupled growth factor receptor mediated activation of the MAPK pathway. Such a pathway had been implicated in proliferation, transformation, and oncogenesis.

The RGS genes, clones h16395 and m1975, were identified in a human spleen cDNA library and a mouse spleen cDNA library, respectively. The first of these genes, clone h16395, encodes a 2.2 Kb RNA transcript having the corresponding cDNA set forth in SEQ ID NO: 1. This transcript encodes a 235 amino acid protein (SEQ ID NO: 2) having a molecular weight of approximately 27.5 kDa.

The second of these genes, clone m1975, encodes a 2.2 Kb RNA transcript having the corresponding cDNA set forth in SEQ ID NO: 3. This transcript also encodes a 235 amino acid protein (SEQ ID NO: 4) having a molecular weight of approximately 27.5 kDa. This mouse RGS protein shares 84% identity with the human RGS protein disclosed in SEQ ID NO: 2 as determined by the Clustal method.

Both of these RGS proteins have N-terminal (amino acids 1–81) and C-terminal (amino acids 202–235) sequences that appear to be unique. The proteins comprise an RGS domain that spans amino acids 82–201. The RGS domain of each of these clones contains 10/11 RGS4 residues (amino acids 107, 109, 111, 112, 152, 154, 183, 187, 188, and 191 of SEQ ID Nos: 2 and 4) that make direct contact with $G_{\alpha i}$ and 18/23 RGS4 residues (amino acids 83, 90, 100, 103, 104, 115, 116, 138, 139, 142, 143, 151, 152, 184, 189, 192, 193, and 198 of SEQ ID Nos: 2 and 4) that form the hydrophobic core of the RGS domain. Furthermore, the carboxyl location of the RGS domain is consistent with RGSs known to act as GTPase activating proteins (GAPs) for $G_\alpha$ proteins.

Figure 2:
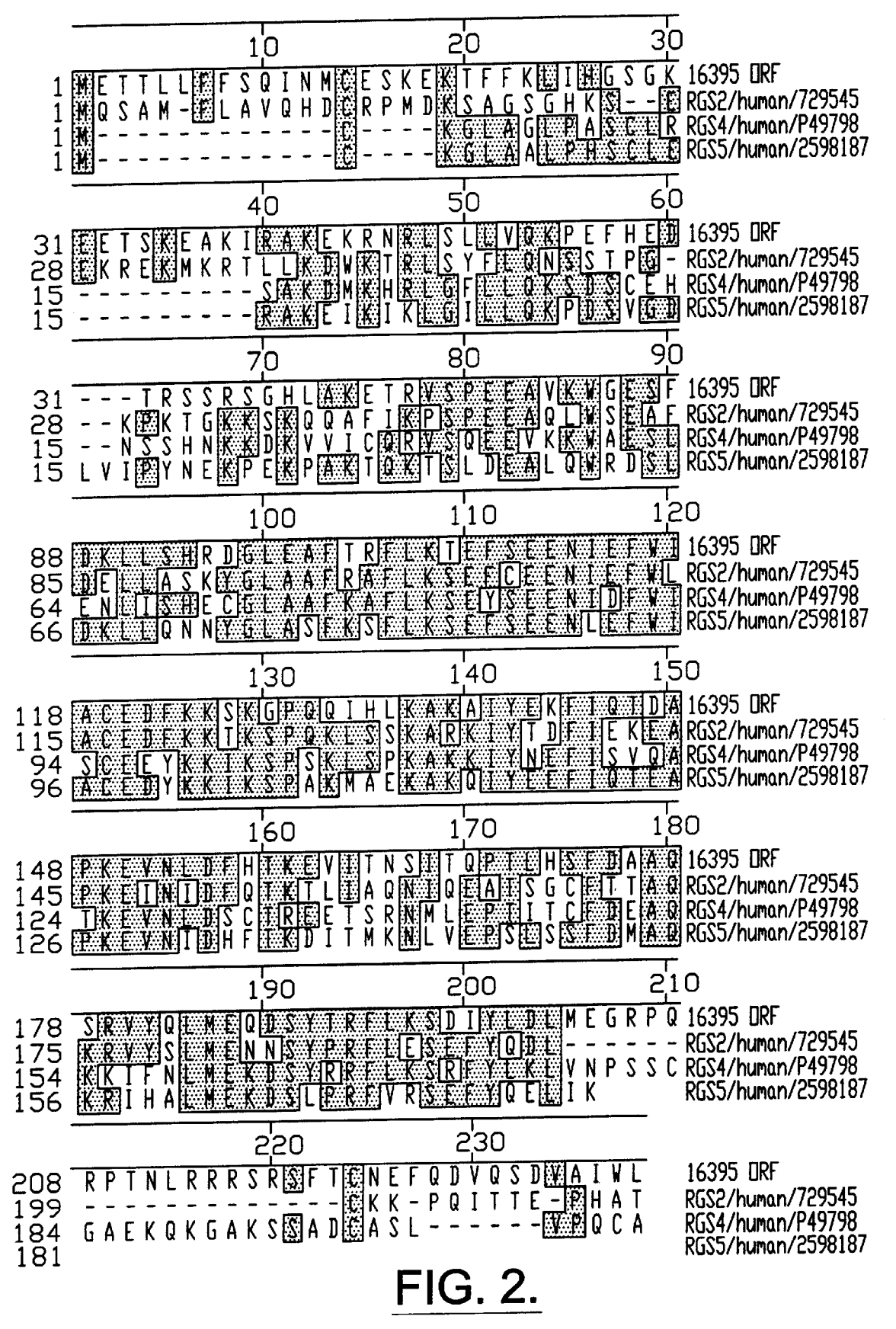

The amino terminal ends of the proteins (amino acids 0–15) are hydrophobic in nature and are important for targeting to the cellular location of $G_\alpha$ proteins. Furthermore, the hydrophobic amino-end of h16395/m1975 is consistent with several other "short-form" RGSs including RGS 1, 2, 4, 5, 8, and RATH/A28-RGS14/RGSr/RGS16. m1975/h16395 share closest homology to human RGS5 protein (about 44% sequence identity for the human sequence) (see FIG. 2). It has been shown that RGSs 4, 5, and 16 contain a plasma membrane signal sequence within this region, which may be involved in targeting the RGS to the $G_\alpha$ protein cellular location. Hence, the hydrophobic amino end of h16395/m1975 may be important for localizing these RGSs to their site of cellular function. Interestingly, "long-form" (RGS3, 6, 7, 9, 11, 12, and 14) and some "short-form" RGSs (GAIP, RGZ1, RGS10 and 13) lack a hydrophobic amino-end, but usually contain other domains that may play a role in cellular targeting.

Two plasmids containing overlapping clones, designated Eph16395A and Eph16395B, for the h16395 DNA were deposited with American Type Culture Collection (ATCC), 10801 University Blvd., Manassas, Va., on Jan. 14, 1999, and assigned Accession Numbers 207049 and 207050, respectively. Eph16395A comprises nucleotides 1 to 801 of h16395 and Eph16395B comprises nucleotides 802 to 1355 of h16395. It is noted, however, that clones Eph16395A and Eph16395B contain common sequences at the regions where they overlap. Eph16395B overlaps Eph16395A from nucleotide 595 to nucleotide 801. One of skill in the art by sequencing the clones and aligning the overlap may obtain the entire sequence of h16395.

A plasmid containing the insert for the m1975, designated Epm1975, was deposited with American Type Culture Collection (ATCC), 10801 University Blvd., Manassas, Va., on Jan. 14, 1999, and assigned Accession Number 207048.

These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The RGS sequences of the invention are members of a family of molecules (the "RGS family") having conserved functional features. As described above, the members of the family comprise an RGS domain. The term "family" when referring to the proteins and nucleic acid molecules of the invention is intended to mean two or more proteins or nucleic acid molecules having sufficient amino acid or nucleotide sequence identity as defined herein. Such family members can be naturally occurring and can be from either the same or different species. For example, a family can contain a first protein of murine origin and a homologue of that protein of human origin, as well as a second, distinct protein of human origin and a murine homologue of that protein. Members of a family may also have common functional characteristics.

Preferred RGS polypeptides of the present invention have an amino acid sequence sufficiently identical to the amino acid sequence of SEQ ID NO:2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75%, 80% identity, more preferably 85%, 90%, 95%, or 98% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, only exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul et al. (1990) *Proc. Natl. Acad. Sci. USA* 87:2264, modified as in Karlin and Altschul (1993) *Proc. Natl. Acad. Sci USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to RGS nucleic acid molecules of the invention. BLAST protein searches can be performed with the XBLAST program, score=50, wordlength=3, to obtain amino acid sequences homologous to RGS protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller et al. (1988) *CABIOS* 4:11–17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

Accordingly, another embodiment of the invention features isolated RGS proteins and polypeptides having an RGS protein activity. As used interchangeably herein, a "RGS protein activity", "biological activity of an RGS protein", or "functional activity of an RGS protein" refers to an activity exerted by an RGS protein, polypeptide, or nucleic acid molecule on an RGS responsive cell as determined in vivo, or in vitro, according to standard assay techniques. An RGS activity can be a direct activity, such as an association with or an enzymatic activity on a second protein, or an indirect activity, such as a cellular signaling activity mediated by interaction of the RGS protein with a second protein. In a preferred embodiment, an RGS activity includes at least one or more of the following activities: (1) modulating (stimulating and/or enhancing or inhibiting) cellular proliferation, differentiation, and/or function, particularly that of immune cells (e.g., tissue macrophages, mast cells, and plasma cells) and hematological cells (e.g., lymphocytes, monocytes, erythrocytes, megakaryocytes, neutrophils, eosinophils, and basophils) and/or progenitors or precursors of these cells; (2) modulating immune and inflammatory responses, particularly T-lymphocyte responses; (3) modulating chemoattractant-induced cell migration and adhesion; (4) modulating G-protein signaling; (5) regulating $G_{\alpha i}$-stimulated pathways; (6) acting as GTPase-activating proteins; (7) mediating desensitization process of receptors, particularly G-protein coupled receptors; (8) binding an RGS ligand; (9) inducing and/or maintaining tolerance in both transplant and autoimmune diseases; (10) modulating the proliferation, differentiation, and/ or function of megakaryocytes and/or platelets; (11) modulating platelet morphology, migration, aggregation, degranulation, and/or function; (12) mediating and/or modulating platelet adhesion and aggregation; and (13) modulating tumor formation, tumor cell migration, and/or tumor cell metastasis.

An "isolated" or "purified" RGS nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules, excludes isolated chromosomes. For example, in various embodiments, the isolated RGS nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. An RGS protein that is substantially free of cellular material includes preparations of RGS protein having less than about 30%, 20%, 10%, or 5% (by dry weight) of non-RGS protein (also referred to herein as a "contaminating protein"). When the RGS protein or biologically active portion thereof is recombinantly produced, preferably, culture medium represents less than about 30%, 20%, 10%, or 5% of the volume of the protein preparation. When RGS protein is produced by chemical synthesis, preferably the protein preparations have less than about 30%, 20%, 10%, or 5% (by dry weight) of chemical precursors or non-RGS chemicals.

Various aspects of the invention are described in further detail in the following subsections.

I. Isolated Nucleic Acid Molecules

One aspect of the invention pertains to isolated nucleic acid molecules comprising nucleotide sequences encoding RGS proteins or biologically active portions thereof, as well as nucleic acid molecules sufficient for use as hybridization probes to identify RGS-encoding nucleic acids (e.g., RGS mRNA) and fragments for use as PCR primers for the amplification or mutation of RGS nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the RGS proteins of the present invention include sequences set forth in SEQ ID NOs: 1 and 3, the nucleotide sequences included in the plasmids deposited with the ATCC as Accession Numbers (the "cDNA of ATCC 207048" for the mouse, or "the DNA of ATCC 207049 and 207050" for the human"), and complements thereof. For purposes of the human sequence the entire coding sequence for the RGS protein can be obtained from sequencing the overlapping clones deposited with the ATCC and assigned ATCC Nos: 207049 and 207050. By "complement" is intended a nucleotide sequence that is sufficiently complementary to a given nucleotide sequence such that it can hybridize to the given nucleotide sequence to thereby form a stable duplex. The corresponding amino acid sequences for the RGS proteins encoded by these nucleotide sequences are set forth in SEQ ID NOs: 2 and 4, respectively.

Nucleic acid molecules that are fragments of these RGS nucleotide sequences are also encompassed by the present invention. By "fragment" is intended a portion of the nucleotide sequence encoding an RGS protein of the invention. A fragment of an RGS nucleotide sequence may encode a biologically active portion of an RGS protein, or it may be a fragment that can be used as a hybridization probe or PCR primer using methods disclosed below. A biologically active portion of an RGS protein can be prepared by isolating a portion of one of the RGS nucleotide sequences of the invention, expressing the encoded portion of the RGS protein (e.g., by recombinant expression in vitro), and assessing the activity of the encoded portion of the RGS protein.

It is recognized that isolated fragments include any contiguous sequence not disclosed prior to the invention as well as sequences that are substantially the same and that are not disclosed. When a sequence is not disclosed prior to the invention, fragments of an RGS nucleotide sequence comprise at least 15, 16, 18, 20, or 30 nucleotides in length and hybridize to the nucleotide sequence of SEQ ID Nos: 1 or 3 under stringent conditions. For example, for h16395, nucleotides 1–23, 275–303, and 732–791 are not disclosed prior to the invention. Other regions of the nucleotide sequence may comprise fragments of various sizes, depending upon potential homology with previously disclosed sequences. For example, the nucleotide sequence from about 24 to about 274 encompasses fragments greater than 236 or 240 nucleotides, the nucleotide sequence from about 304 to about 792 encompasses fragments greater than 19 or 20 nucleotides, the nucleotide sequence from about 792 to about 1400 encompasses fragments greater than 537, 540, or 550 nucleotides, and the nucleotide sequence from about 1400 to the end of the molecule encompasses fragments greater than 307, 310 or 320 nucleotides. In these embodiments, depending on the region, the nucleic acid can be at least 15, 20, 30, 40, 50, 75, 100, 325, 350, 375, 400, 425, 450, 500, 550, 600, 650, 700, 800, 900, 1,000, or 1,100 nucleotides, or up to the number of nucleotides present in a full-length RGS nucleotide sequence disclosed herein (for example, 2,217 or 1,164 nucleotides for SEQ ID NO:1 or 3, respectively).

A fragment of an RGS nucleotide sequence that encodes a biologically active portion of an RGS protein of the invention will encode at least 15, 25, 30, 50, 100, 125, 150, 175, 200, or 225 contiguous amino acids, or up to the total number of amino acids present in a full-length RGS protein of the invention (for example, 235 amino acids, SEQ ID NOs: 2 and 4). Fragments of an RGS nucleotide sequence that are useful as hybridization probes for PCR primers generally need not encode a biologically active portion of an RGS protein.

Nucleic acid molecules that are variants of the RGS nucleotide sequences disclosed herein are also encompassed by the present invention. "Variants" of the RGS nucleotide sequences include those sequences that encode the RGS proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the RGS proteins disclosed in the present invention as discussed above. Generally, nucleotide sequence variants of the invention will have at least 45%, 55%, 65%, 75%, 85%, 95%, or 98% identity to the nucleotide sequences disclosed herein. A variant RGS nucleotide sequence will encode an RGS protein that has an amino acid sequence having at least 45%, 55%, 65%, 75%, 85%, 95%, or 98% identity to an amino acid sequence of an RGS protein disclosed herein.

In addition to the RGS nucleotide sequences shown in SEQ ID NOs: 1 and 3, the nucleotide sequence of the cDNA of ATCC 207048, and the DNA of ATCC 207049 and 207050, it will be appreciated by those skilled in the art that DNA sequence polymorphisms that lead to changes in the amino acid sequences of RGS proteins may exist within a population (e.g., the human population). Such genetic polymorphism in an RGS gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding an RGS protein, preferably a mammalian RGS protein. As used herein, the phrase "allelic variant" refers to a nucleotide sequence that occurs at an RGS locus or to a polypeptide encoded by the nucleotide sequence. Such natural allelic variations can typically result in 1–5% variance in the nucleotide sequence of the RGS gene. Any and all such nucleotide variations and resulting amino acid polymorphisms or variations in an RGS sequence that are the result of natural allelic variation and that do not alter the functional activity of RGS proteins are intended to be within the scope of the invention.

Moreover, nucleic acid molecules encoding RGS proteins from other species (RGS homologues), which have a nucleotide sequence differing from that of the RGS sequences disclosed herein, are intended to be within the scope of the invention. Nucleic acid molecules corresponding to natural allelic variants and homologues of the RGS DNA sequences of the invention can be isolated based on their identity to the mouse or human RGS nucleic acids disclosed herein using the sequences of the invention, or a portion thereof, as a hybridization probe according to standard hybridization techniques under stringent hybridization conditions as disclosed below.

In addition to naturally-occurring allelic variants of the RGS sequence that may exist in the population, the skilled artisan will further appreciate that changes can be introduced by mutation into the nucleotide sequences of the invention thereby leading to changes in the amino acid sequence of the encoded RGS protein, without altering the biological activity of the RGS protein. Thus, an isolated nucleic acid molecule encoding an RGS protein having a sequence that differs from that of SEQ ID NO: 2 or 4, can be created by introducing one or more nucleotide substitutions, additions, or deletions into the nucleotide sequences disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of an RGS protein (e.g., the sequence of SEQ ID NO: 2 or 4) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, such as amino acid residues residing within a conserved motif, such as the RGS domain, where such residues are essential for protein activity.

Alternatively, variant RGS nucleotide sequences can be made by introducing mutations randomly along all or part of an RGS coding sequence, such as by saturation mutagenesis, and the resultant mutants can be screened for RGS biological activity to identify mutants that retain activity. Following mutagenesis, the encoded protein can be expressed recombinantly, and the activity of the protein can be determined using standard assay techniques.

Thus the nucleotide sequences of the invention include those sequences disclosed herein as well as fragments and variants thereof. The RGS nucleotide sequences of the invention, and fragments and variants thereof, can be used as probes and/or primers to identify and/or clone RGS homologues in other cell types, e.g., from other tissues, as well as RGS homologues from other mammals. Such probes can be used to detect transcripts or genomic sequences encoding the same or identical proteins. These probes can be used as part of a diagnostic test kit for identifying cells or tissues that misexpress an RGS protein, such as by measuring levels of an RGS-encoding nucleic acid in a sample of cells from a subject, e.g., detecting RGS mRNA levels or determining whether a genomic RGS gene has been mutated or deleted.

In this manner, methods such as PCR, hybridization, and the like can be used to identify such sequences having substantial identity to the sequences of the invention. See, e.g., Sambrook et al. (1989) *Molecular Cloning: Laboratory Manual* (2d ed., Cold Spring Harbor Laboratory Press, Plainview, N.Y.) and Inns, et al. (1990) *PCR Protocols: A Guide to Methods and Applications* (Academic Press, N.Y.). RGS nucleotide sequences isolated based on their sequence identity to the RGS nucleotide sequences set forth herein or to fragments and variants thereof are encompassed by the present invention.

In a hybridization method, all or part of a known RGS nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes maybe genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known RGS nucleotide sequences disclosed herein. Degenerate primers designed on the basis of conserved nucleotides or amino acid residues in a known RGS nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of an RGS nucleotide sequence of the invention or a fragment or variant thereof. Preparation of probes for hybridization is generally known in the art and is disclosed in Sambrook et al. (1989) *Molecular Cloning. A Laboratory Manual* (2d ed., Cold Spring Harbor Laboratory Press, Plainview, N.Y.), herein incorporated by reference.

For example, in one embodiment, a previously unidentified RGS nucleic acid molecule hybridizes under stringent conditions to a probe that is a nucleic acid molecule comprising one of the RGS nucleotide sequences of the invention or a fragment thereof. In another embodiment, the previously unknown RGS nucleic acid molecule is at least 300, 325, 350, 375, 400, 425, 450, 500, 550, 600, 650, 700, 800, 900, 1000, 2,000, 3,000, 4,000 or 5,000 nucleotides in length and hybridizes under stringent conditions to a probe that is a nucleic acid molecule comprising one of the RGS nucleotide sequences disclosed herein or a fragment thereof.

Accordingly, in another embodiment, an isolated previously unknown RGS nucleic acid molecule of the invention is at least 300, 325, 350, 375, 400, 425, 450, 500, 550, 600, 650, 700, 800, 900, 1000, 1,100, 1,200, 1,300, or 1,400 nucleotides in length and hybridizes under stringent conditions to a probe that is a nucleic acid molecule comprising one of the nucleotide sequences of the invention, preferably the coding sequence set forth in SEQ ID NO:1 or 3, the cDNA of ATCC 207048, the DNA of ATCC 207049 and 207050, or a complement, fragment, or variant thereof.

As used herein, the term "hybridizes under stringent conditions" is intended to describe conditions for hybridization and washing under which nucleotide sequences having at least 60%, 65%, 70%, preferably 75% identity to each other typically remain hybridized to each other. Such stringent conditions are known to those skilled in the art and can be found in *Current Protocols in Molecular Biology* (John Wiley & Sons, New York (1989)), 6.3.1–6.3.6. A preferred, non-limiting example of stringent hybridization condition is hybridization in 6× sodium chloride/sodium citrate (SSC) at about 45° C., followed by one or more washes in 0.2×SSC, 0.1% SDS at 50–65° C. In another preferred embodiment, stringent conditions comprise hybridization in 6×SSC at 42° C., followed by washing with 1×SSC at 55° C. Preferably, an isolated nucleic acid molecule that hybridizes under stringent conditions to an RGS sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Thus, in addition to the RGS nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the RGS nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire RGS coding strand, or to only a portion thereof, e.g., all or part of the protein coding region (or open reading frame). An antisense nucleic acid molecule can be antisense to a noncoding region of the coding strand of a nucleotide sequence encoding an RGS protein. The noncoding regions are the 5' and 3' sequences that flank the coding region and are not translated into amino acids.

Given the coding-strand sequences encoding an RGS protein disclosed herein (e.g., SEQ ID NOs: 1 and 3), antisense nucleic acids of the invention can be designed according to the rules of Watson and Crick base pairing. The antisense nucleic acid molecule can be complementary to the entire coding region of RGS mRNA, but more preferably is an oligonucleotide that is antisense to only a portion of the coding or noncoding region of RGS mRNA. For example, the antisense oligonucleotide can be complementary to the region surrounding the translation start site of RGS mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an RGS protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an $\alpha$-anomeric nucleic acid molecule. An $\alpha$-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhofff et al. (1988) *Nature* 334:585–591)) can be used to catalytically cleave RGS mRNA transcripts to thereby inhibit translation of RGS mRNA. A ribozyme having specificity for an RGS-encoding nucleic acid can be designed based upon the nucleotide sequence of an RGS cDNA disclosed herein (e.g., SEQ ID NO:1 or 3). See, e.g., Cech et al., U.S. Pat. No. 4,987,071; and Cech et al., U.S. Pat. No. 5,116,742. Alternatively, RGS mRNA can be used to select a catalytic RNA having a specific ribonuclease activity from a pool of RNA molecules. See, e.g., Bartel et al. (1993) *Science* 261:1411–1418.

The invention also encompasses nucleic acid molecules that form triple helical structures. For example, RGS gene expression can be inhibited by targeting nucleotide sequences complementary to the regulatory region of the RGS protein (e.g., the RGS promoter and/or enhancers) to form triple helical structures that prevent transcription of the RGS gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of an RGS molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996), supra).

In another embodiment, PNAs of an RGS molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357–63; Mag. et al. (1989) *Nucleic Acids Res.* 17:5973; and Peterser et al. (1975) *Bioorganic Med. Chem. Lett.* 5:1119.

II. Isolated RGS Proteins and Anti-RGS Antibodies

RGS proteins are also encompassed within the present invention. By "RGS protein" is intended proteins having the amino acid sequence set forth in SEQ ID NO: 2 or 4 as well as fragments, biologically active portions, and variants thereof.

"Fragments" or "biologically active portions" include polypeptide fragments suitable for use as immunogens to raise anti-RGS antibodies. Fragments include peptides comprising amino acid sequences sufficiently identical to or derived from the amino acid sequences of an RGS protein of the invention and exhibiting at least one activity of an RGS protein, but which include fewer amino acids than the full-length RGS proteins disclosed herein. Typically, biologically active portions comprise a domain or motif with at least one activity of the RGS protein. A biologically active portion of an RGS protein can be a polypeptide that is, for example, 10, 25, 50, 100 or more amino acids in length. Such biologically active portions can be prepared by recombinant techniques and evaluated for one or more of the functional activities of a native RGS protein. As used here, a fragment comprises at least 6 contiguous amino acids, such as from amino acids 1–110. The invention encompasses other fragments, however, such as any fragment in the protein greater than 10, 12, 15, or 16 amino acids.

By "variants" is intended proteins or polypeptides having an amino acid sequence that is at least about 45%, 55%, 65%, preferably about 75%, 85%, 95%, or 98% identical to the amino acid sequence of SEQ ID NO: 2 or 4. Variants also include polypeptides encoded by the cDNA insert of the plasmid deposited with ATCC as Accession Number 207048 for the mouse, and by the DNA sequence obtained from the plasmids deposited with the ATCC as Accession Numbers 207049 and 207050 for the human, or polypeptides encoded by a nucleic acid molecule that hybridizes to a nucleic acid molecule of SEQ ID NO: 1, 3, or a complement thereof, under stringent conditions. Such variants generally retain the functional activity of the RGS proteins of the invention. Variants include polypeptides that differ in amino acid sequence due to natural allelic variation or mutagenesis.

The invention also provides RGS chimeric or fusion proteins. As used herein, an RGS "chimeric protein" or "fusion protein" comprises an RGS polypeptide operably linked to a non-RGS polypeptide. A "RGS polypeptide" refers to a polypeptide having an amino acid sequence corresponding to an RGS protein, whereas a "non-RGS polypeptide" refers to a polypeptide having an amino acid sequence corresponding to a protein that is not substantially identical to the RGS protein, e.g., a protein that is different from the RGS protein and which is derived from the same or a different organism. Within an RGS fusion protein, the RGS polypeptide can correspond to all or a portion of an RGS protein, preferably at least one biologically active portion of an RGS protein. Within the fusion protein, the term "operably linked" is intended to indicate that the RGS polypeptide and the non-RGS polypeptide are fused in-frame to each other. The non-RGS polypeptide can be fused to the N-terminus or C-terminus of the RGS polypeptide.

One useful fusion protein is a GST-RGS fusion protein in which the RGS sequences are fused to the C-terminus of the GST sequences. Such fusion proteins can facilitate the purification of recombinant RGS proteins.

In yet another embodiment, the fusion protein is an RGS-immunoglobulin fusion protein in which all or part of an RGS protein is fused to sequences derived from a member of the immunoglobulin protein family. The RGS-immunoglobulin fusion proteins of the invention can be incorporated into pharmaceutical compositions and administered to a subject to inhibit an interaction between an RGS ligand and an RGS protein on the surface of a cell, thereby suppressing RGS-mediated signal transduction in vivo. The RGS-immunoglobulin fusion proteins can be used to affect the bioavailability of an RGS cognate ligand. Inhibition of the RGS ligand/RGS interaction may be useful therapeutically, both for treating proliferative and differentiative disorders and for modulating (e.g., promoting or inhibiting) cell survival. Moreover, the RGS-immunoglobulin fusion proteins of the invention can be used as immunogens to produce anti-RGS antibodies in a subject, to purify RGS ligands, and in screening assays to identify molecules that inhibit the interaction of an RGS protein with an RGS ligand.

Preferably, an RGS chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-lnterscience, N.Y.). Moreover, an RGS-encoding nucleic acid can be cloned into a commercially available expression vector such that it is linked in-frame to an existing fusion moiety.

Variants of the RGS proteins can function as either RGS agonists (mimetics) or as RGS antagonists. Variants of the RGS protein can be generated by mutagenesis, e.g., discrete point mutation or truncation of the RGS protein. An agonist of the RGS protein can retain substantially the same, or a subset, of the biological activities of the naturally occurring form of the RGS protein. An antagonist of the RGS protein can inhibit one or more of the activities of the naturally occurring form of the RGS protein by, for example, competitively binding to a downstream or upstream member of a cellular signaling cascade that includes the RGS protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the RGS proteins.

Variants of the RGS protein that function as either RGS agonists or as RGS antagonists can be identified by screening combinatorial libraries of mutants, e.g., truncation mutants, of the RGS protein for RGS protein agonist or antagonist activity. In one embodiment, a variegated library of RGS variants is generated by combinatorial mutagenesis at the nucleic acid level and is encoded by a variegated gene library. A variegated library of RGS variants can be produced by, for example, enzymatically ligating a mixture of synthetic oligonucleotides into gene sequences such that a degenerate set of potential RGS sequences is expressible as individual polypeptides, or alternatively, as a set of larger fusion proteins (e.g., for phage display) containing the set of RGS sequences therein. There are a variety of methods that can be used to produce libraries of potential RGS variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential RGS sequences. Methods for synthesizing degenerate oligonucleotides are known in the art (see, e.g., Narang (1983) *Tetrahedron* 39:3; Itakura et al. (1984) *Ann. Rev. Biochem.* 53:323; Itakura et al. (1984) *Science* 198:1056; Ike et al. (1983) *Nucleic Acid Res.* 11:477).

In addition, libraries of fragments of the RGS protein coding sequence can be used to generate a variegated population of RGS fragments for screening and subsequent selection of variants of an RGS protein. In one embodiment, a library of coding sequence fragments can be generated by treating a double-stranded PCR fragment of an RGS coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the RGS protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of RGS proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify RGS variants (Arkin et al. (1992) *Proc. Natl. Acad. Sci. USA* 89:7811–7815; Delgrave et al. (1993) *Protein Engineering* 6(3):327–331).

An isolated RGS polypeptide of the invention can be used as an immunogen to generate antibodies that bind RGS proteins using standard techniques for polyclonal and monoclonal antibody preparation. The full-length RGS protein can be used or, alternatively, the invention provides antigenic peptide fragments of RGS proteins for use as immunogens. The antigenic peptide of an RGS protein comprises at least 8, preferably 10, 15, 20, or 30 amino acid residues of the amino acid sequence shown in SEQ ID NO: 2 or 4 and encompasses an epitope of an RGS protein such that an antibody raised against the peptide forms a specific immune complex with the RGS protein. Preferred epitopes encompassed by the antigenic peptide are regions of a RGS protein that are located on the surface of the protein, e.g., hydrophilic regions.

Accordingly, another aspect of the invention pertains to anti-RGS polyclonal and monoclonal antibodies that bind an RGS protein. Polyclonal anti-RGS antibodies can be prepared by immunizing a suitable subject (e.g., rabbit, goat, mouse, or other mammal) with an RGS immunogen. The anti-RGS antibody titer in the immunized subject can be monitored over time by standard techniques, such as with an enzyme linked immunosorbent assay (ELISA) using immobilized RGS protein. At an appropriate time after immunization, e.g., when the anti-RGS antibody titers are highest, antibody-producing cells can be obtained from the subject and used to prepare monoclonal antibodies by standard techniques, such as the hybridoma technique originally described by Kohler et al. (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., N.Y.; and Lerner (1981) *Yale J. Biol Med.* 54:387–402).

Alternative to preparing monoclonal antibody-secreting hybridomas, a monoclonal anti-RGS antibody can be identified and isolated by screening a recombinant combinatorial immunoglobulin library (e.g., an antibody phage display library) with an RGS protein to thereby isolate immunoglobulin library members that bind the RGS protein. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-RGS antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86101533 and WO 87/02671; European Patent Application Nos. 184,187, 171, 496, 125,023, and 173,494; U.S. Pat. Nos. 4,816,567 and 5,225,539; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559); Morrison (1985) *Science* 229:1202–1207; Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, e.g., Lonberg et al. (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Fremont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-RGS antibody (e.g., monoclonal antibody) can be used to isolate RGS proteins by standard techniques, such as affinity chromatography or immunoprecipitation. An anti-RGS antibody can facilitate the purification of natural RGS protein from cells and of recombinantly produced RGS protein expressed in host cells. Moreover, an anti-RGS antibody can be used to detect RGS protein (e.g., in a cellular lysate or cell supernatant) in order to evaluate the abundance and pattern of expression of the RGS protein. Anti-RGS antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (I) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84:Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding an RGS protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, e.g., Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., RGS proteins, mutant forms of RGS proteins, fusion proteins, etc.).

The recombinant expression vectors of the invention can be designed for expression of RGS protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, Calif.), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow et al. (1989) *Virology* 170:31–39)); yeast cells (examples of vectors for expression in yeast *S. cereivisiae* include pYepSec1 (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Cailf.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)).

Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T-cell receptors (Winoto and Baltimore (1989) *EMBO J.* 8:729–733) and immunoglobulins (Banerji et al. (1983) *Cell* 33:729–740; Queen et al. (1983) *Cell* 33:741–748), neuron-specific promoters (e.g., the neurofilament promoter; Byrne et al. (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Patent Publication No. 264,166). Developmentally-regulated promoters are also encompassed, for example the murine hox promoters (Kessel et al. (1990) *Science* 249:374–379), the $\alpha$-fetoprotein promoter (Campes et al. (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to RGS mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics* 1:1.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding an RGS protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) RGS protein. Accordingly, the invention further provides methods for producing RGS protein using the host cells of the invention. In one embodiment, the method comprises culturing the host cell of the invention, into which a recombinant expression vector encoding an RGS protein has been introduced, in a suitable medium such that RGS protein is produced. In another embodiment, the method further comprises isolating RGS protein from the medium or the host cell.

The host cells of the invention can also be used to produce nonhuman transgenic animals. For example, in one embodiment, a host cell of the invention is a fertilized oocyte or an embryonic stem cell into which RGS-coding sequences have been introduced. Such host cells can then be used to create nonhuman transgenic animals in which exogenous RGS sequences have been introduced into their genome or homologous recombinant animals in which endogenous RGS sequences have been altered. Such animals are useful for studying the function and/or activity of RGS genes and proteins and for identifying and/or evaluating modulators of RGS activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous RGS gene has been altered by homologous recombination between the endogenous gene and an exogenous DNA molecule introduced into a cell of the animal, e.g., an embryonic cell of the animal, prior to development of the animal.

A transgenic animal of the invention can be created by introducing RGS-encoding nucleic acid into the male pronuclei of a fertilized oocyte, e.g., by microinjection, retroviral infection, and allowing the oocyte to develop in a pseudopregnant female foster animal. The RGS cDNA sequence can be introduced as a transgene into the genome of a nonhuman animal. Alternatively, a homologue of the mouse RGS gene can be isolated based on hybridization and used as a transgene. Intronic sequences and polyadenylation signals can also be included in the transgene to increase the efficiency of expression of the transgene. A tissue-specific regulatory sequence(s) can be operably linked to the RGS transgene to direct expression of RGS protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the RGS transgene in its genome and/or expression of RGS mRNA in tissues or cells of the animals. A transgenic founder animal can then be used to breed additional animals carrying the transgene. Moreover, transgenic animals carrying a transgene encoding RGS gene can further be bred to other transgenic animals carrying other transgenes.

To create a homologous recombinant animal, one prepares a vector containing at least a portion of an RGS gene or a homologue of the gene into which a deletion, addition, or substitution has been introduced to thereby alter, e.g., functionally disrupt, the RGS gene. In a preferred embodiment, the vector is designed such that, upon homologous recombination, the endogenous RGS gene is functionally disrupted (i.e., no longer encodes a functional protein; also referred to as a "knock out" vector). Alternatively, the vector can be designed such that, upon homologous recombination, the endogenous RGS gene is mutated or otherwise altered but still encodes functional protein (e.g., the upstream regulatory region can be altered to thereby alter the expression of the endogenous RGS protein). In the homologous recombination vector, the altered portion of the RGS gene is flanked at its 5' and 3' ends by additional nucleic acid of the RGS gene to allow for homologous recombination to occur between the exogenous RGS gene carried by the vector and an endogenous RGS gene in an embryonic stem cell. The additional flanking RGS nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced RGS gene has homologously recombined with the endogenous RGS gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810–813 and PCT Publication Nos. WO 97/07668 and WO 97/07669.

IV. Pharmaceutical Compositions

The RGS nucleic acid molecules, RGS proteins, and anti-RGS antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradernal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor ELF™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., an RGS protein or anti-RGS antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

Antibodies or antibodies conjugated to therapeutic moieties can be administered to an individual alone or in combination with cytotoxic factor(s), chemotherapeutic drug(s), and/or cytokine(s). If the latter, preferably, the antibodies are administered first and the cytotoxic factor(s), chemotherapeutic drug(s) and/or cytokine(s) are administered thereafter within 24 hours. The antibodies and cytotoxic factor(s), chemotherapeutic drug(s) and/or cytokine(s) can be administered by multiple cycles depending upon the clinical response of the patient. Further, the antibodies and cytotoxic factor(s), chemotherapeutic drug(s) and/or cytokine(s) can be administered by the same or separate routes, for example, by intravenous, intranasal or intramuscular administration. Cytotoxic factors include, but are not limited to, TNF-$\alpha$, TNF-$\beta$, IL-1, IFN-$\gamma$ and IL-2. Chemotherapeutic drugs include, but are not limited to, 5-fluorouracil (5FU), vinblastine, actinomycin D, etoposide, cisplatin, methotrexate and doxorubicin. Cytolines include, but are not limited to, IL-2, IL-3, IL-4, IL-5, IL-6, IL-7, IL-8, IL-9, IL-10 and IL-12.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology); (c) predictive medicine (e.g. diagnostic assays, prognostic assays, monitoring clinical trials, and pharmacogenomics); and (d) methods of treatment (e.g., therapeutic and prophylactic). The isolated nucleic acid molecules of the invention can be used to express RGS protein (e.g., via a recombinant expression vector in a host cell in gene therapy applications), to detect RGS mRNA (e.g. in a biological sample) or a genetic lesion in an RGS gene, and to modulate RGS activity. In addition, the RGS proteins can be used to screen drugs or compounds that modulate the immune response as well as to treat disorders characterized by insufficient or excessive production of RGS protein or production of RGS protein forms that have decreased or aberrant activity compared to RGS wild type protein. In addition, the anti-RGS antibodies of the invention can be used to detect and isolate RGS proteins and modulate RGS activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to RGS proteins or have a stimulatory or inhibitory effect on, for example, RGS expression or RGS activity.

The test compounds of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer-Drug Des.* 12:145). Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds maybe presented in solution (e.g. Houghten (1992) *Bio/Techniques* 13:412–421), or on beads (Lam (1991) *Nature* 354:82–84), chips (Fodor (1993) *Nature* 364:555–556), bacteria (U.S. Pat. No. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869), or phage (Scott etal. (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to the RGS protein can be accomplished, for example, by coupling the test compound with a radioisotope or enzymatic label such that binding of the test compound to the RGS protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the RGS protein to bind to or interact with an RGS target molecule. By "target molecule" is intended a molecule with which an RGS protein binds or interacts in nature. In a preferred embodiment, the ability of the RGS protein to bind to or interact with an RGS target molecule can be determined by monitoring the activity of the target molecule. For example, the activity of the target molecule can be monitored by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., an RGS-responsive regulatory element operably linked to a nucleic acid encoding a detectable marker, e.g., luciferase), or detecting a cellular response, for example, cellular differentiation or cell proliferation.

In yet another embodiment, an assay of the present invention is a cell-free assay comprising contacting an RGS protein or biologically active portion thereof with a test compound and determining the ability of the test compound to bind to the RGS protein or biologically active portion thereof Binding of the test compound to the RGS protein can be determined either directly or indirectly as described above. In a preferred embodiment, the assay includes contacting the RGS protein or biologically active portion thereof with a known compound that binds RGS protein to form an assay mixture, contacting the assay mixture with a test compound, and determining the ability of the test compound to preferentially bind to RGS protein or biologically active portion thereof as compared to the known compound.

In another embodiment, an assay is a cell-free assay comprising contacting RGS protein or biologically active portion thereof with a test compound and determining the ability of the test compound to modulate (e.g., stimulate or inhibit) the activity of the RGS protein or biologically active portion thereof. Determining the ability of the test compound to modulate the activity of an RGS protein can be accomplished, for example, by determining the ability of the RGS protein to bind to an RGS target molecule as described above for determining direct binding. In an alternative embodiment, determining the ability of the test compound to modulate the activity of an RGS protein can be accomplished by determining the ability of the RGS protein to further modulate an RGS target molecule. For example, the catalytic/enzymatic activity of the target molecule on an appropriate substrate can be determined as previously described.

In yet another embodiment, the cell-free assay comprises contacting the RGS protein or biologically active portion thereof with a known compound that binds an RGS protein to form an assay mixture, contacting the assay mixture with a test compound, and determining the ability of the test compound to preferentially bind to or modulate the activity of an RGS target molecule.

In the above-mentioned assays, it may be desirable to immobilize either an RGS protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/RGS fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or RGS protein, and the mixture incubated under conditions conducive to complex formation (e.g. at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of RGS binding or activity determined using standard techniques.

Other techniques for immobilizing proteins on matrices can also be used in the screening assays of the invention. For example, either RGS protein or its target molecule can be immobilized utilizing conjugation of biotin and streptavidin. Biotinylated RGS molecules or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with an RGS protein or target molecules but which do not interfere with binding of the RGS protein to its target molecule can be derivatized to the wells of the plate, and unbound target or RGS protein trapped in the wells by antibody conjugation. Methods for detecting such complexes, in addition to those described above for the GST-immobilized complexes, include immunodetection of complexes using antibodies reactive with the RGS protein or target molecule, as well as enzyme-linked assays that rely on detecting an enzymatic activity associated with the RGS protein or target molecule.

In another embodiment, modulators of RGS expression are identified in a method in which a cell is contacted with a candidate compound and the expression of RGS mRNA or protein in the cell is determined relative to expression of RGS mRNA or protein in a cell in the absence of the candidate compound. When expression is greater (statistically significantly greater) in the presence of the candidate compound than in its absence, the candidate compound is identified as a stimulator of RGS mRNA or protein expression. Alternatively, when expression is less (statistically significantly less) in the presence of the candidate compound than in its absence, the candidate compound is identified as an inhibitor of RGS mRNA or protein expression. The level of RGS mRNA or protein expression in the cells can be determined by methods described herein for detecting RGS mRNA or protein.

In yet another aspect of the invention, the RGS proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with RGS protein ("RGS-binding proteins" or "RGS-bp") and modulate RGS activity. Such RGS-binding proteins are also likely to be involved in the propagation of signals by the RGS proteins as, for example, upstream or downstream elements of the RGS pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial RGS gene sequences of the invention can be used to map their respective RGS genes on a chromosome, thereby facilitating the location of gene regions associated with genetic disease. Computer analysis of RGS sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the RGS sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919–924). Somatic cell hybrids containing only fragments of human chromosomes can also be produced by using human chromosomes with translocations and deletions.

Other mapping strategies that can similarly be used to map an RGS sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma et al. (1988) *Human Chromosomes: A Manual of Basic Techniques* (Pergamon Press, N.Y.). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Another strategy to map the chromosomal location of RGS genes uses RGS polypeptides and fragments and sequences of the present invention and antibodies specific thereto. This mapping can be carried out by specifically detecting the presence of an RGS polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains. For examples of this technique, see Pajunen et al. (1988) *Cytogenet. Cell Genet.* 47:37–41 and Van Keuren et al. (1986) *Hum. Genet.* 74:34–40. Alternatively, the presence of an RGS polypeptide in the somatic cell hybrids can be determined by assaying an activity or property of the polypeptide, for example, enzymatic activity, as described in Bordelon-Riser et al. (1979) *Somatic Cell Genetics* 5:597–613 and Owerbach et al. (1978) *Proc. Natl. Acad. Sci. USA* 75:5640–5644.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the RGS gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The RGS sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the RGS sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The RGS sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO:1 or 3 can comfortably provide positive individual identification with a panel of perhaps 10 to 1,000 primers that each yield a noncoding amplified sequence of 100 bases. If predicted coding sequences, such as those in SEQ ID NO:1 or 3 are used, a more appropriate number of primers for positive individual identification would be 500 to 2,000.

3. Use of Partial RGS Sequences in Forensic Biology

DNA-based identification techniques can also be used in forensic biology. In this manner, PCR technology can be used to amplify DNA sequences taken from very small biological samples such as tissues, e.g., hair or skin, or body fluids, e.g. blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:1 or 3 are particularly appropriate for this use as greater numbers of polymorphisms occur in the noncoding regions, making it easier to differentiate individuals using this technique. Examples of polynucleotide reagents include the RGS sequences or portions thereof, e.g., fragments derived from the noncoding regions of SEQ ID NO:1 or 3 having a length of at least 20 or 30 bases.

The RGS sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such RGS probes, can be used to identify tissue by species and/or by organ type.

In a similar fashion, these reagents, e.g., RGS primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting RGS protein and/or nucleic acid expression as well as RGS activity, in the context of a biological sample. An exemplary method for detecting the presence or absence of RGS proteins in a biological sample involves obtaining a biological sample from a test subject and contacting the biological sample with a compound or an agent capable of detecting RGS protein or nucleic acid (e.g., mRNA, genomic DNA) that encodes RGS protein such that the presence of RGS protein is detected in the biological sample. Results obtained with a biological sample from the test subject may be compared to results obtained with a biological sample from a control subject.

A preferred agent for detecting RGS mRNA or genomic DNA is a labeled nucleic acid probe capable of hybridizing to RGS mRNA or genomic DNA. The nucleic acid probe can be, for example, a full-length RGS nucleic acid, such as the nucleic acid of SEQ ID NO:1 or 3, or a portion thereof, such as a nucleic acid molecule of at least 15, 30, 50, 100, 250, or 500 nucleotides in length and sufficient to specifically hybridize under stringent conditions to RGS MRNA or genomic DNA. Other suitable probes for use in the diagnostic assays of the invention are described herein.

A preferred agent for detecting RGS protein is an antibody capable of binding to RGS protein, preferably an antibody with a detectable label. Antibodies can be polyclonal, or more preferably, monoclonal. An intact antibody, or a fragment thereof (e.g., Fab or $F(ab')_2$)can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect RGS mRNA, protein, or genomic DNA in a biological sample in vitro as well as in vivo. For example, in vitro techniques for detection of RGS mRNA include Northern hybridizations and in situ hybridizations. In vitro techniques for detection of RGS protein include enzyme linked immunosorbent assays (ELISAs), Western blots, immunoprecipitations, and immunofluorescence. In vitro techniques for detection of RGS genomic DNA include Southern hybridizations. Furthermore, in vivo techniques for detection of RGS protein include introducing into a subject a labeled anti-RGS antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

The invention also encompasses kits for detecting the presence of RGS proteins in a biological sample (a test sample). Such kits can be used to determine if a subject is suffering from or is at increased risk of developing a disorder associated with aberrant expression of RGS protein (e.g., an immunological disorder). For example, the kit can comprise a labeled compound or agent capable of detecting RGS protein or mRNA in a biological sample and means for determining the amount of an RGS protein in the sample (e.g., an anti-RGS antibody or an oligonucleotide probe that binds to DNA encoding an RGS protein, e.g., SEQ ID NO:1 or 3). Kits can also include instructions for observing that the tested subject is suffering from or is at risk of developing a disorder associated with aberrant expression of RGS sequences if the amount of RGS protein or mRNA is above or below a normal level.

For antibody-based kits, the kit can comprise, for example: (1) a first antibody (e.g., attached to a solid support) that binds to RGS protein; and, optionally, (2) a second, different antibody that binds to RGS protein or the first antibody and is conjugated to a detectable agent. For oligonucleotide-based kits, the kit can comprise, for example: (1) an oligonucleotide, e.g., a detectably labeled oligonucleotide, that hybridizes to an RGS nucleic acid sequence or (2) a pair of primers useful for amplifying an RGS nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of RGS proteins.

2. Prognostic Assays

The methods described herein can furthermore be utilized as diagnostic or prognostic assays to identify subjects having or at risk of developing a disease or disorder associated with RGS protein, RGS nucleic acid expression, or RGS activity. Prognostic assays can be used for prognostic or predictive purposes to thereby prophylactically treat an individual prior to the onset of a disorder characterized by or associated with RGS protein, RGS nucleic acid expression, or RGS activity.

Thus, the present invention provides a method in which a test sample is obtained from a subject, and RGS protein or nucleic acid (e.g., mRNA, genomic DNA) is detected, wherein the presence of RGS protein or nucleic acid is diagnostic for a subject having or at risk of developing a disease or disorder associated with aberrant RGS expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g. agents of a type that decrease RGS activity) to effectively treat a disease or disorder associated with aberrant RGS expression or activity. In this manner, a test sample is obtained and RGS protein or nucleic acid is detected. The presence of RGS protein or nucleic acid is diagnostic for a subject that can be administered the agent to treat a disorder associated with aberrant RGS expression or activity.

The methods of the invention can also be used to detect genetic lesions or mutations in an RGS gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion or mutation characterized by at least one of an alteration affecting the integrity of a gene encoding an RGS-protein, or the misexpression of the RGS gene. For example, such genetic lesions or mutations can be detected by ascertaining the existence of at least one of: (1) a deletion of one or more nucleotides from an RGS gene; (2) an addition of one or more nucleotides to an RGS gene; (3) a substitution of one or more nucleotides of an RGS gene; (4) a chromosomal rearrangement of an RGS gene; (5) an alteration in the level of a messenger RNA transcript of an RGS gene; (6) an aberrant modification of an RGS gene, such as of the methylation pattern of the genomic DNA; (7) the presence of a non-wild-type splicing pattern of a messenger RNA transcript of an RGS gene; (8) a non-wild-type level of an RGS-protein; (9) an allelic loss of an RGS gene; and (10) an inappropriate post-translational modification of an RGS-protein. As described herein, there are a large number of assay techniques known in the art that can be used for detecting lesions in an RGS gene. Any cell type or tissue, preferably peripheral blood leukocytes, in which RGS proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the RGS-gene (see, e.g., Abravaya et al. (1995) *Nucleic Acids Res.* 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an RGS gene from a sample cell can be identified by alterations in restriction enzyme cleavage patterns of isolated test sample and control DNA digested with one or more restriction endonucleases. Moreover, the use of sequence specific ribozymes (see, e.g. U.S. Pat. No. 5,498,531) can be used to score for the presence of specific mutations by development or loss of a ribozyme cleavage site.

In other embodiments, genetic mutations in an RGS molecule can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). In yet another embodiment, any of a variety of sequencing reactions known in the art can be used to directly sequence the RGS gene and detect mutations by comparing the sequence of the sample RGS gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the RGS gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in RGS cDNAs obtained from samples of cells. See, e.g., Hsu et al. (1994) *Carcinogenesis* 15:1657–1662. According to an exemplary embodiment, a probe based on an RGS sequence, e.g., a wild-type RGS sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in RGS genes. For example, single-strand conformation polymorphism (SSCP) maybe used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125–144; Hayashi (1992) *Genet. Anal Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it maybe desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnose patients exhibiting symptoms or family history of a disease or illness involving an RGS gene.

3. Pharmacogenomics

Agents, or modulators that have a stimulatory or inhibitory effect on RGS activity (e.g., RGS gene expression) as identified by a screening assay described herein, can be administered to individuals to treat (prophylactically or therapeutically) disorders associated with aberrant RGS activity as well as to modulate the phenotype of an immune response. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of RGS protein, expression of RGS nucleic acid, or mutation content of RGS genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g. N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of RGS protein, expression of RGS nucleic acid, or mutation content of RGS genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an RGS modulator, such as a modulator identified by one of the exemplary screening assays described herein.

4. Monitoring of Effects During Clinical Trials

Monitoring the influence of agents (e.g. drugs, compounds) on the expression or activity of RGS genes (e.g., the ability to modulate aberrant cell proliferation and/or differentiation) can be applied not only in basic drug screening but also in clinical trials. For example, the effectiveness of an agent, as determined by a screening assay as described herein, to increase or decrease RGS gene expression, protein levels, or protein activity, can be monitored in clinical trials of subjects exhibiting decreased or increased RGS gene expression, protein levels, or protein activity. In such clinical trials, RGS expression or activity and preferably that of other genes that have been implicated in for example, a cellular proliferation disorder, can be used as a marker of the immune responsiveness of a particular cell.

For example, and not by way of limitation, genes that are modulated in cells by treatment with an agent (e.g., compound, drug, or small molecule) that modulates RGS activity (e.g., as identified in a screening assay described herein) can be identified. Thus, to study the effect of agents on cellular proliferation disorders, for example, in a clinical trial, cells can be isolated and RNA prepared and analyzed for the levels of expression of RGS genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of RGS genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g. an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of an RGS protein, mRNA, or genomic DNA in the preadministration sample; (3) obtaining one or more postadministration samples from the subject; (4) detecting the level of expression or activity of the RGS protein, MRNA, or genomic DNA in the postadministration samples; (5) comparing the level of expression or activity of the RGS protein, mRNA, or genomic DNA in the preadministration sample with the RGS protein, mRNA, or genomic DNA in the postadministration sample or samples; and (vi) altering the administration of the agent to the subject accordingly to bring about the desired effect, i.e., for example, an increase or a decrease in the expression or activity of an RGS protein.

C. Methods of Treatment

The present invention provides for both prophylactic and therapeutic methods of treating a subject at risk of (or susceptible to) a disorder or having a disorder associated with aberrant RGS expression or activity. Additionally, the compositions of the invention find use in modulating the T-lymphocyte response and granulocyte and platelet functions. Thus, therapies for immune, respiratory, and hematological disorders are encompassed herein.

1. Prophylactic Methods

In one aspect, the invention provides a method for preventing in a subject a disease or condition associated with an aberrant RGS expression or activity by administering to the subject an agent that modulates RGS expression or at least one RGS gene activity. Subjects at risk for a disease that is caused, or contributed to, by aberrant RGS expression or activity can be identified by, for example, any or a combination of diagnostic or prognostic assays as described herein. Administration of a prophylactic agent can occur prior to the manifestation of symptoms characteristic of the RGS aberrancy, such that a disease or disorder is prevented or, alternatively, delayed in its progression. Depending on the type of RGS aberrancy, for example, an RGS agonist or RGS antagonist agent can be used for treating the subject. The appropriate agent can be determined based on screening assays described herein.

2. Therapeutic Methods

Another aspect of the invention pertains to methods of modulating RGS expression or activity for therapeutic purposes. The modulatory method of the invention involves contacting a cell with an agent that modulates one or more of the activities of RGS protein activity associated with the cell. An agent that modulates RGS protein activity can be an agent as described herein, such as a nucleic acid or a protein, a naturally-occurring cognate ligand of an RGS protein, a peptide, an RGS peptidomimetic, or other small molecule. In one embodiment, the agent stimulates one or more of the biological activities of RGS protein. Examples of such stimulatory agents include active RGS protein and a nucleic acid molecule encoding an RGS protein that has been introduced into the cell. In another embodiment, the agent inhibits one or more of the biological activities of RGS protein. Examples of such inhibitory agents include anti-sense RGS nucleic acid molecules and anti-RGS antibodies.

These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of an RGS protein or nucleic acid molecule. In one embodiment, the method involves administering an agent (e.g., an agent identified by a screening assay described herein), or a combination of agents, that modulates (e.g. upregulates or downregulates) RGS expression or activity. In another embodiment, the method involves administering an RGS protein or nucleic acid molecule as therapy to compensate for reduced or aberrant RGS expression or activity.

Stimulation of RGS activity is desirable in situations in which an RGS protein is abnormally downregulated and/or in which increased RGS activity is likely to have a beneficial effect. Conversely, inhibition of RGS activity is desirable in situations in which RGS activity is abnormally upregulated and/or in which decreased RGS activity is likely to have a beneficial effect.

This invention is further illustrated by the following examples, which should not be construed as limiting.

EXAMPLES

Example 1

Cloning Strategy

Using the database mining strategy for expressed sequence tags (ESTs) with similarity to the Regulator of G protein Signaling (RGS) domain ESTs, jthsa069c04t1 (human spleen cDNA library) and jtmea012d11t1 (mouse megakaryocyte cDNA library) were identified for human 16395 (h16395) and the mouse orthologue 1975 (m1975), respectively. 5'-RACE of human or mouse spleen Marathon-ready cDNA libraries (Clontech) was used to complete full-length cloning.

Example 2 h16395 and m1975 cDNA Sequences

For h16395 a nucleotide sequence of 2156 nucleotides (nt) was obtained which included the entire open reading frame, polyadenylation sequence and poly-A tail. The nucleotide sequence length was in agreement with the mRNA transcript size of approximately 2.4 kb. An open reading frame of 235 amino acids (MW=27.6 kDa) was identified for both h16395 and m1975, with the RGS domain being present between amino acids 82 and 201 (FIGS. 1A and B). 84% identity was observed between h16395 and m1975 (FIG. 1C). Importantly, this high degree of identity was observed within and outside the RGS domain of h16395 and m1975, indicating they are orthologues. Typically, different RGSs only exhibit a high degree of identity within the RGS domain. Using the Kyte Doolittle hydrophilicity analysis, hydrophobic NH2— (approximately 1–15 amino acids (aa)) and COOH-ends (approximately 210–235 aa) were identified.

No proteins were found to be identical to h16395 or m1975 sequences in the Nucleotide and Preview Nucleotide, MAPEST, DBEST, and Patent; or the Patent, PDB, PNU, and Protein databases using TBlastN or BlastP, respectively. Furthermore, no matches were identified when the NH2— (1–81 aa) or COOH— (202–235 aa) ends were used to search the protein databases with BlastP. However, RGS protein matches showing similarity to the RGS domains (82–201 aa) of h16395 and m1975 were identified in the databases. Of those identified, the top 6 matches included mRGS2 (59%), hRGS2 (58%), hRGS5 (55%), mRGS5 (55%), hRGS4 (52%), and mRGS4 (52%), with the percent identity for the RGS domain shown in parentheses. The RGS domain of h16395/m1975 is present at the COOH-end, and contains the majority of residues that have been shown in RGS4 to make direct contact with Gαi or that form the RGS domain hydrophobic core.

Example 3

Modulation of G-Protein-Mediated Signal Transduction

Mutations in the yeast SST2 gene, which encodes an RGS-containing gene product, cause increased sensitivity and defective desensitization to signal transduction induced by alpha factor mating pheromone. The results described below demonstrate complementation of SST2 mutations in yeast by the h16395 protein, and indicate that 16395 acts to modulate G-protein-mediated signal transduction. Functional complementation of an SST2 mutation by h16395 provides a convenient yeast-based bioassay for 16395 function. Such a bioassay can, for example, be used to identify molecules that are agonists or antagonists of h16395.

Plasmids containing the h16395 coding sequence were constructed as follows: The h16395 coding sequence was cloned into yeast expression vectors pYADE4 and pYPGE2. pYADE4 contains the ADH2 promoter and pYPGE2 contains the PGK promoter. On media where glucose is the sole carbon source, such as the media used in this experiment, the PGK promoter is reported to be 17 times stronger than the ADH2 promoter (Brunelli and Pall, 1993, Yeast, 9:1299–1308).

Oligonucleotides D1 (5'-AGT CCG GGA TCC AAA AAA ATG GAA ACA ACA TTG CTT TTC TTT-3', SEQ ID NO:5) and D2 (5'-CCG TAC GTC GAC TTA TAA CCA AAT GGC AAC ATC TGA TTG-3', SEQ ID NO:6) were used to amplify the entire predicted 708 base pair coding sequence of h16395 predicted to encode a 235 (plus stop codon) amino acid protein. Restriction endonuclease sites BamHI and Sal I were engineered into the oligonucleotides to allow the cloning of the PCR fragment encoding the h16395 protein into yeast expression vectors pYADE4 and pYPGE2 (Brunelli and Pall (1993) *Yeast*, 9:1299–1308). In addition, the sequence AAAAAA was introduced immediately upstream of the initiator ATG codon to promote efficient translation in yeast (Hinnebusch and Liebman (1991) *The Molecular Biology and Cellular Biology of the Yeast Saccharomyces: Genome Dynamics, Protein Synthesis, and Energetics* (Cold Spring Harbor Laboratory Press, Plainview, N.Y.), pp. 627–735). The PCR product coding 16395 was doubly digested with BamHI and Sal I and ligated after column purification (PCR Select II columns, 5' to 3') into pYADE4 and pYPGE2 doubly digested with BamHI and Sal I. Ligation reactions were transformed into the TOP10F' *E. coli* stain (Gibco BRL). One *E. coli* clone containing the 16395 coding sequence in pYADE4 was isolated and named p10B2 and one *E. coli* clone containing the 16395 coding sequence in pYPGE2 was isolated and named p10A4.

Standard yeast medium containing synthetic complete medium lacking L-tryptophan was prepared and yeast genetic manipulation was performed as described (Sherman (1991) *Meth. Enzymol.*, 194:3–21). Yeast transformations were performed using standard protocols (Gietz et a. (1992) *Nucleic Acids Res.*, 20:1425. Ito et al, (1983) *J. Bacteriol.*, 153:163–168).

Isogenic $SST2^+$ (MF42) and $SST2^-$ (MF41) strains were transformed with pYADE4, pYPGE2, p10B2, and p10A4. Transformants were selected on synthetic complete medium lacking L-tryptophan. Transformants were picked from each transformation and were used for further experimentation. The transformants were designated as follows: MF41 transformed with pYADE4 (MF41:pYADE4); MF41 transformed with pYPGE2 (ME41:pYPGE2); MF41 transformed with p10B2 (MF41:p10B2); MF41 transformed with p10A4 (MF41:p10A4); MF42 transformed with pYADE4 (MF42:pYADE4); MF42 transformed with YPGE2 (MF42:pYPGE2); MF42 transformed with p10B2 (MF42:p10B2); and MF42 transformed with p10A4 (MF42:p10A4).

The MF41 and MF42 transformants were subjected to desensitization assays, performed as follows: MF41 and MF42 transformants were grown to saturation overnight in liquid synthetic complete medium lacking L-tryptophan. Each culture was diluted 1:40 into 2 ml of liquid synthetic complete medium lacking L-tryptophan which was added to 2 ml of 1% (wt/vol) agar dissolved in water and warmed to 50° C. The resulting cell suspension was plated on a synthetic complete medium lacking L-tryptophan plate and allowed to solidify. Sterile BBL blank paper ¼₀ inch disks (BBL Microbiology Systems) were spotted with 10.0, 1.0, or 0.1 $\mu$g of synthetic alpha factor (Sigma) and were arrayed on top of the solidified agar medium. The diameter of the halos of growth arrested cells surrounding the filter disks containing alpha factor were photographed and measured after 24 hours of growth.

The results obtained from the desensitization assays are summarized below in Table 1. Ten $\mu$g of alpha factor resulted in an approximate 34 mm zone of growth inhibition of the SST2-strain transformed with either pYADE4 or pYPGE2 (MF41:pYADE4 and MF41:pYPGE2), whereas 10 $\mu$g of alpha factor resulted in a 22 mm zone of growth inhibition of the $SST2^-$ strain expressing h16395 under the control of the ADH2 promoter (MF41:p10B2). This decreased zone of inhibition suggests that h16395 under the control of the ADH2 promoter functionally complements the $SST2^-$ mutation. Such complementation of an $SST2^-$ mutation by h16395 is strong evidence that h16395 has GAP activity towards GPA1 and more generally towards G-protein alpha subunits.

In the $SST2^-$ strain expressing h16395 under the control of the strong PGK promoter (MF41:p10A4), 10 $\mu$g of alpha factor resulted in a 14 mm zone of growth inhibition. The experimental results indicate that in the absence of the SST2 protein, the h16395 protein can significantly block the transduction of the signal produced by 10 $\mu$g of alpha factor and supports the hypothesis that h16395 acts as a GAP on GPA1. This experimental result also indicates that the alpha factor resistance phenotype conferred by h16395 expression plasmids is a function of the level of h16395 expression, i.e., the stronger PGK promoter causes a stronger phenotype than the weaker ADH2 promoter.

No significant difference was observed between pYADE4 or pYPGE2 (MF42:pYADE4and MF42:pYPGE2) alone, as compared to constructs containing 16395 (MF42:p10B2 and MF42:p10A4) when the $SST2^+$ strain was used, This suggested that endogenous levels of SST2 were sufficient to allow growth in the presence of alpha factor under the experimental conditions used.

TABLE 1

| | Amount of alpha factor added to disk | | |
|---|---|---|---|
| Strain Name | 10 $\mu$g | 1 $\mu$g | 0.1 $\mu$g |
| MF41:pYADE4 | 33 | 25 | 14 |
| MF41:pYPGE2 | 35 | 24 | 16 |
| MF41:p10B2 | 22 | 13 | 8 |
| MF41:p10A4 | 14 | 8 | None |
| MF42:pYADE4 | 14 | None | None |
| MF42:pYPGE2 | 13 | None | None |
| MF42:p10B2 | 13 | None | None |
| MF42:p10A4 | 13 | None | None |

Diameters of growth inhibition zones in mm caused by filter disks impregnated with different quantities of alpha factor are shown, in centimeters, below each alpha factor concentration.

Example 4

Expression of h16395

An mRNA transcript of approximately 2.4 kb was detected for h16395 or m1975 by Northern blot analysis. h16395 was most abundant in peripheral blood leukocytes and fetal liver. Lower levels of expression were detected in the spleen, bone marrow, and liver; and to a lesser extent in the heart, colon, and placenta. Transcripts were detected in T-cells, monocytes, and granulocytes by RT-PCR. 3'-UTR probes were used to avoid cross-hybridization with other RSG proteins. m1975 exhibited an expression pattern consistent with h16395. The presence of the h16395/m1975 transcript in non-lymphoid tissues maybe due to blood contamination.

Quantitative expression of the novel h16395 was measured by TaqMan® quantitative PCR (Perkin Elmer Applied Biosystems) in cDNA prepared from the following normal human tissues: lymph node, spleen, thymus, brain, lung, skeletal muscle, fetal liver, and normal and fibrotic liver; the following primary cells: resting and phytohemaglutinin (PHA) activated peripheral blood mononuclear cells (PBMC); resting and PHA activated $CD3^+$ cells, $CD4^+$ and $CD8^+$ T cells; Th1 and Th2 cells stimulated for six or 48 hours with anti-CD3 antibody; resting and lipopolysaccharide (LPS) activated CD19+ B cells; CD34+ cells from mobilized peripheral blood (mPB CD34+), adult resting bone marrow (ABM CD34+), granulocyte colony stimulating factor (G-CSF) mobilized bone marrow (mBM CD34+), and neonatal umbilical cord blood (CB CD34+); G-CSF mobilized peripheral blood leukocytes (mPB leukocytes); CD34− cells from mobilized peripheral blood (mPB CD34−), neonatal umbilical cord blood (CB CD34−), G-CSF mobilized bone marrow (mBM CD34−), and adult resting bone marrow (ABM CD34−); CD 14+ cells; granulocytes; megakaryocytes generated in vitro from cytokine stimulated bone marrow CD34+ cells (BM megakaryocytes); megakaryocytes generated in vitro using peripheral blood CD34+ cells stimulated with SF and TPO (mPB megakaryocytes); and erythroblasts generated in vitro from peripheral blood CD34+ cells stimulated with SF and EPO. Transformed human cell lines included K526, an erythroleukemia; HL60, an acute promyelocytic leukemia; Jurkat, a T cell leukemia; HEK 293, epithelial cells from embryonic kidney transformed with adenovirus 5 DNA; MOLT4, a T lymphoblast; and Hep3B hepatocellular liver carcinoma cells cultured in normal (Hep3B normal) or reduced oxygen tension (Hep3B hypoxia).

Probes were designed by PrimerExpress software (PE Biosystems) based on the h16395 sequence. The primers and probes for expression analysis of h16395 and β-2 microglobulin were as follows:

h16395 Forward Primer TGACTGAGAATAAGATCCA-
    CATTTGAA                                    (SEQ ID NO:7)

h16395 Reverse Primer CATGTTTCTGTGACCAACAGAAG-
    TACT                                        (SEQ ID NO:8)

h16395 TaqMan Probe TCATTCCTAAGTGAACATGGACGTAC-
    CCAGTT                                      (SEQ ID NO:9)

β-2 microglobulin Forward Primer CACCCCCACTGAAAAA-
    GATGA                                       (SEQ ID NO:10)

β-2 microglobulin Reverse Primer CTTAACTATCTTGGGCTGT-
    GACAAAG                                     (SEQ ID NO:11)

β-2 microglobulin TaqMan Probe TATGCCTGCCGTGTGAAC-
    CACGTG                                      (SEQ ID NO: 12)

The h16395 sequence probe was labeled using FAM (6-carboxyfluorescein), and the β2-microglobulin reference probe was labeled with a different fluorescent dye, VIC. The differential labeling of the target h16395 sequence and internal reference gene thus enabled measurement in the same well. Forward and reverse primers and the probes for both β2-microglobulin and the target h16395 sequence were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target h16395 sequence. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate h16395 expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the h16395 sequence is normalized by subtracting the Ct value of the β-2 microglobulin gene to obtain a ΔCt value using the following formula: $\Delta Ct = Ct_{h16395} - Ct\beta\text{-}2_{microglobulin}$. Expression is then calibrated against a cDNA sample showing a comparatively low level of expression of the h16395sequence. The ΔCt value for the calibrator sample is then subtracted from ΔCt for each tissue sample according to the following formula: $\Delta\Delta Ct = \Delta Ct_{sample} - \Delta Ct_{calibrator}$. Relative expression is then calculated using the arithmetic formula given by $2^{-\Delta\Delta Ct}$. Expression of the target h16395 sequence in each of the tissues tested was then graphically represented as discussed in more detail below.

FIG. 3 shows expression of h16395 as determined in a broad panel of tissues and cell lines as described above, relative to expression in Th1 (M4) cells stimulated for 48 hours with anti-CD3 antibody. The results indicate that expression of h16395 was detectable in all normal human tissues tested and highest in hematopoietic cells. The overall highest level of expression was seen in granulocytes, followed by mPB CD34+ cells and fetal liver. Significant expression was also seen in spleen, resting PBMC, mPB leukocytes and CD34− cells, and ABM CD34+ cells and mBM CD34+ cells. Low level expression was shown by CB CD34+ and CD34− cells, ABM CD34− cells and mBM CD34$^{n-}$ cells, CD 14+ cells, as well as the cell lines K562 and Jurkat.

Figure 4:
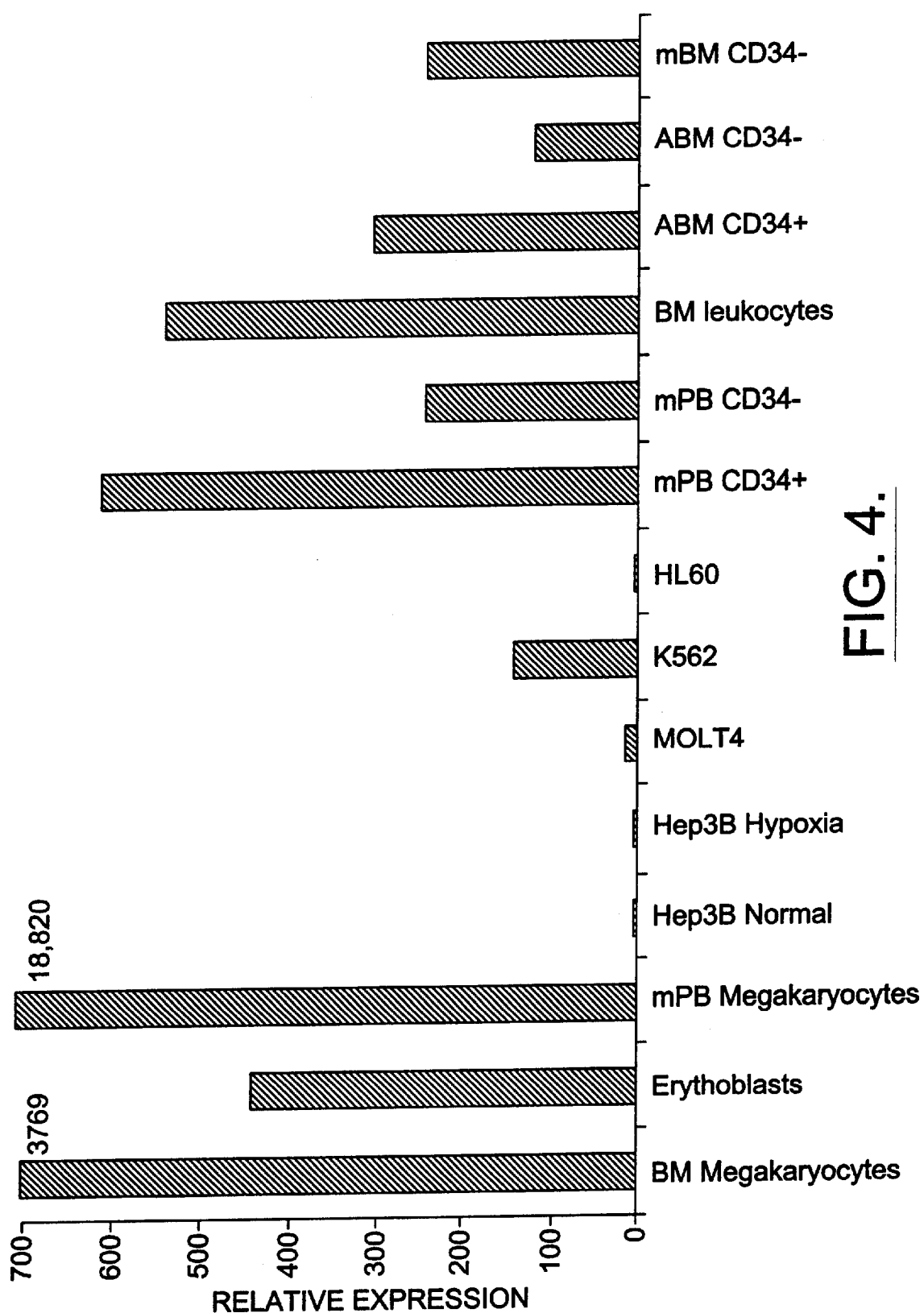
FIG. 4 shows expression of h16395 in hematopoietic cells relative to expression in HL60, and is described further in Example 4.
Figure 5:
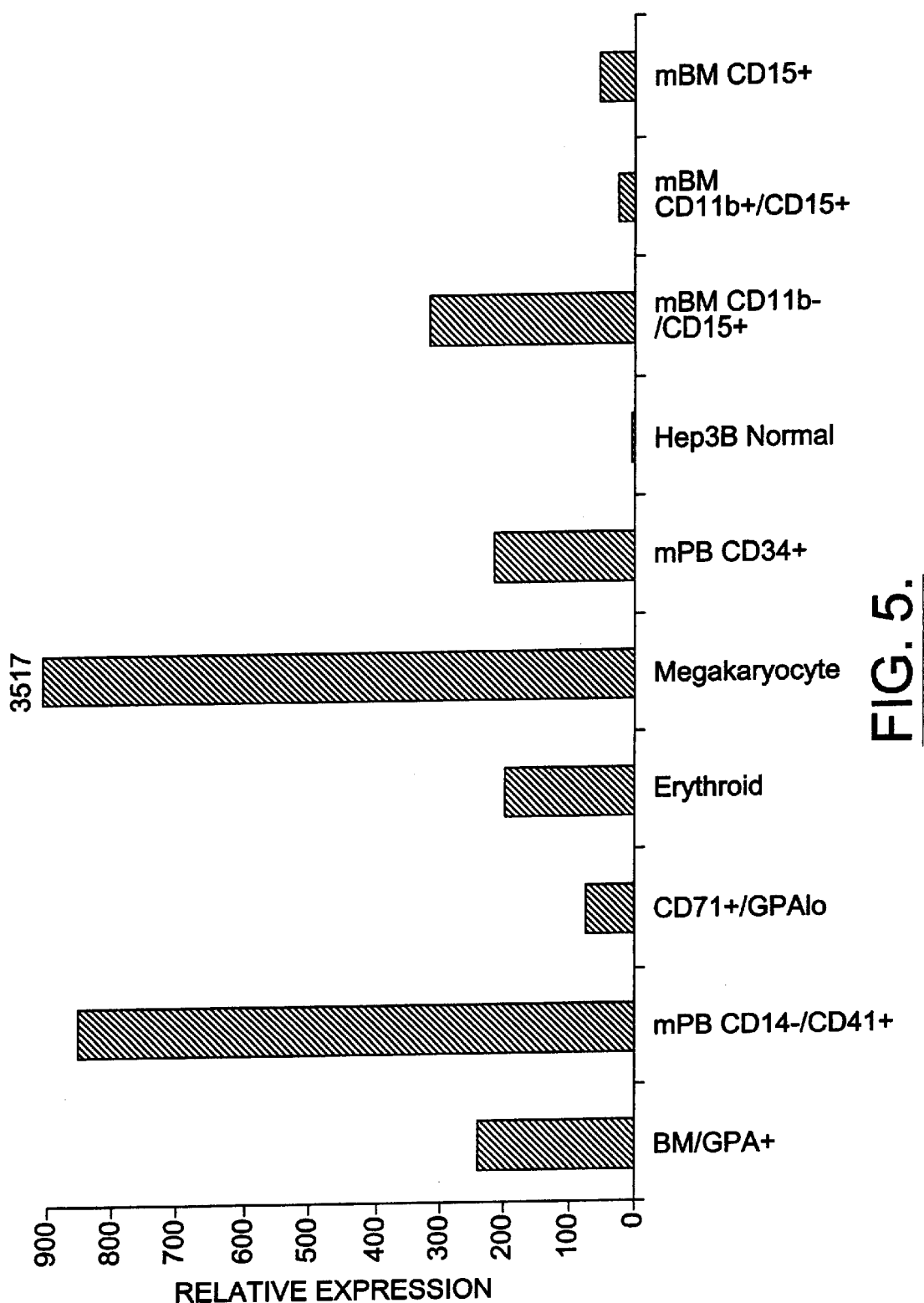
FIG. 5 shows expression of h16395 in hematopoietic cells relative to expression in Hep3B cells, and is described further in Example 4.

The high expression observed among hematopoietic cell populations was reexamined, the results of which are shown in FIG. 4. The highest levels of expression of h16395, relative to expression in HL60, was seen in megakaryocyte progenitors and mature megakaryocytes. The pattern of expression indicates that mRNA synthesis of h16395 increases as hematopoietic progenitors commit to the megakaryocyte lineage and continue to increase throughout megakaryocyte development. FIG. 5 summarizes further examination of h16395 expression in the following cells, relative to Hep3B normal: erythroid lineage cells from bone marrow (BM/GPA+); erythroid progenitors from bone marrow (CD71+/GP/Alo); megakaryocyte progenitors isolated from G-CSF mobilized peripheral blood (CD14−/CD41+); erythroblasts; mPB megakaryocytes; mPB CD34+; bone marrow neutrophil progenitors from volunteers treated with G-CSF (mBM CD11b−/CD15+); bone marrow neutrophils from volunteers treated with G-CSF (mBM CD11b+/CD15+); and bone marrow neutrophil progenitor and mature cells from volunteers treated with G-CSF (mBM CD15+). The results show that the highest level of h16395 was in the mPB megakaryocyte sample, followed by megakaryocyte progenitors (mPB CD14−/CD41+).

The high level of expression of h16395 in megakaryocytes and megakaryocyte progenitors suggest a role for h16395 in hematopoiesis and the development of blood cells, particularly, in the development of megakaryocytes and platelets.

Figure 6:
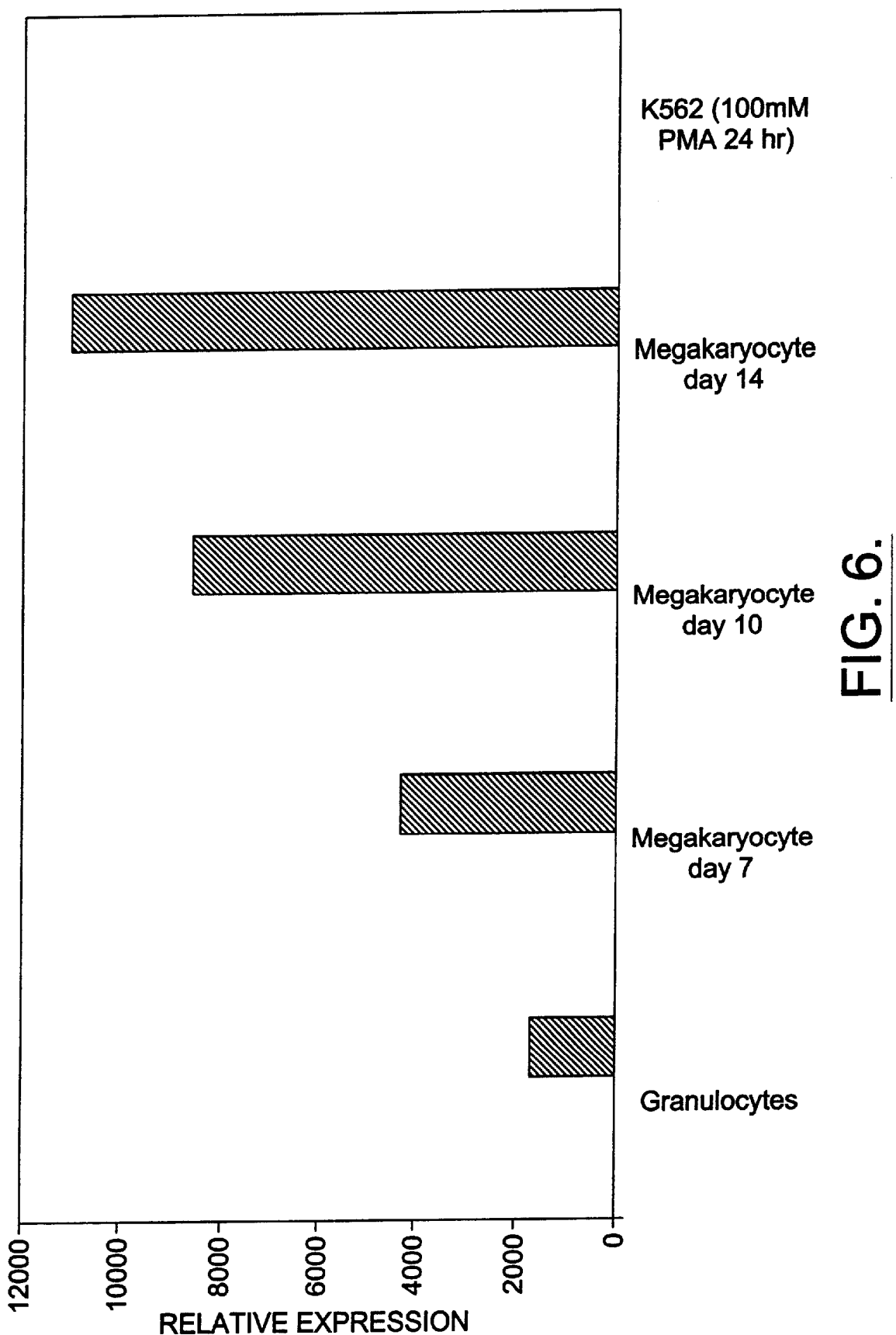
FIG. 6 shows expression of h16395 in granulocytes and different megakaryocyte cultures generated in vitro by SCF and TPO after 4, 10, or 14 days in culture, relative to K562 stimulated with 100 mM PMA for 24 hr, and is described further in Example 4.

FIG. 6 is a summary of the comparative expression of h16395 in granulocytes and different megakaryocyte cultures generated in vitro by SCF and TPO after 4, 10, or 14 days in culture, relative to K562 stimulated with 100 mM PMA for 24 hr. The results show that expression in granulocytes is lower than in any of the megakaryocyte cultures. Although different megakaryocyte cultures were used, the increase in h16395 expression in day 4 to day 10 cultures is consistent with megakaryocyte maturation.

Example 5
Binding Specificity of 16395 to Recombinant Gαi Proteins

The fusion protein GST-16395 binds to $G_{\alpha i-1}$, $G_{\alpha i-2}$, $G_{\alpha i-3}$, and $G_{\alpha o}$ when complexed to GDP-AlF4 sup, but not to GDP. Briefly, the experiment was performed by incubating 1 mg of GST or GST-16395 with 2.5 mg of either $G_{\alpha i-1}$, $G_{\alpha i-2}$, $G_{\alpha i-3}$, or $G_{\alpha o}$ each of which had been pre-complexed to either GDP or GDP-AlF4. Following incubation, the precipitates were then washed and resolved by SDS-PAGE. After transfer, the nitrocellulose membrane was incubated with specific antibodies raised against $G_{\alpha i-1}$, $G_{\alpha i-2}$, $G_{\alpha i-3}$, or $G_{\alpha o}$. Precipitates were identified by Western immunoblot analysis.

GDP-AlF4-activated $G_{\alpha i-1}$, $G_{\alpha i-2}$, $G_{\alpha i-3}$, or $G_{\alpha o}$ were detected in GST-16395 but not GST precipitates. Because AlF4 sup induces a conformation of $G_\alpha$ subunits resembling the transition state recognized by RGSs and leading to GTP hydrolysis, these results demonstrate that 16395 is capable of this RGS function.

Example 6
Inhibition of MAPK Activation In Vitro

Over-expression of 16395 in HEK293 cells expressing the CXCR4 receptor resulted in decreased SDF-1 induced p44/42 MAPK activation as compared to vector control. Briefly, the experiment was performed by transiently transfecting HEK293 cells expressing the CXCR4 receptor with a 16395 construct in pcDNA3.1 (Invitrogen) or the pcDNA3.1 vector alone. After 36 hr expression, the cells were treated for 15 min with the CXCR4 ligand, SDF-1 (stromal cell derived factor 1), or medium alone, then cell extracts were prepared. Phosphorylated MAPK p44/42 was immuno-precipitated using specific antibodies raised against this protein, then incubated with Elk-1 protein, and resolved by SDS-PAGE. After transfer, the nitrocellulose membrane was incubated with a specific antibody raised against phosphorylated Elk-1. Precipitates were identified by Western immunoblot analysis. This downregulation of MAPK activation by 16395 demonstrates a function characteristic of RGSs.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

That which is claimed is:

1. A method for identifying an agent that binds to a polypeptide selected from the group consisting of:
   a) a polypeptide comprising the amino acid sequence of SEQ ID NO: 2 or SEQ ID NO: 4;
   b) a polypeptide comprising an amino acid sequence encoded by the cDNA insert of the plasmid deposited with ATCC as Accession Number 207048; or
   c) a polypeptide comprising an amino acid sequence encoded by the DNA sequence obtained from overlapping clones deposited with ATCC as Accession Numbers 207049 and 207050,
   said method comprising the steps of;
   a) combining an agent to be tested with a composition comprising said polypeptide under conditions suitable for binding; and
   b) detecting the formation of a complex between said agent and said polypeptide.

2. The method of claim 1, wherein the binding of the agent to the polypeptide is detected by a method selected from the group consisting of:
   a) directly detecting the binding of the agent to the polypeptide; and
   b) detecting the binding of the agent to the polypeptide using a competition binding assay.

3. A method for identifying an agent that binds to a host cell expressing a polypeptide selected from the group consisting of:
   a) a polypeptide comprising the amino acid sequence of SEQ ID NO: 2 or SEQ ID NO:4;
   b) a polypeptide comprising an amino acid sequence encoded by the cDNA insert of the plasmid deposited with ATCC as Accession Number 207048; or
   c) a polypeptide comprising an amino acid sequence encoded by the DNA sequence obtained from overlapping clones deposited with ATCC as Accession Numbers 207049 and 207050,
   said method comprising the steps of;
   a) combining an agent to be tested with a composition comprising said host cell expressing said polypeptide under conditions suitable for binding; and
   b) detecting the formation of a complex between said agent and said polypeptide.

4. The method of claim 3, wherein the binding of the agent to the host cell expressing the polypeptide is detected using an assay for detection of a G-protein-mediated signal transduction.

5. The method of claim 4, wherein the agent identified is an agent that inhibits the activity of the polypeptide, and wherein inhibition of said activity results in increased G-protein-mediated signal transduction.

6. The method of claim 3, wherein said host cell is a hematopoietic cell.

7. The method of claim 6, wherein said hematopoietic cell is a megakaryocyte progenitor cell or a mature megakaryocyte.

8. A method for identifying an agent that binds to a polypeptide comprising a fragment of the amino acid sequence of SEQ ID NO:2 or SEQ ID NO:4, wherein said fragment comprises at least 30 contiguous amino acids of SEQ ID NO:2 or SEQ ID NO:4 and has the ability to activate GTPase, said method comprising the steps of:
   a) combining an agent to be tested with a composition comprising said polypeptide under conditions suitable for binding; and b) detecting the formation of a complex between said agent and said polypeptide.

9. The method of claim 8, wherein the binding of the agent to the polypeptide is detected by a method selected from the group consisting of:
   a) directly detecting the binding of the agent to the polypeptide; and
   b) detecting the binding of the agent to the polypeptide using a competition binding assay.

10. A method for identifying an agent that binds to a host cell expressing a polypeptide comprising a fragment of the amino acid sequence of SEQ ID NO:2 or SEQ ID NO:4, wherein said fragment comprises at least 30 contiguous amino acids of SEQ ID NO:2 or SEQ ID NO:4 and has the ability to activate GTPase, said method comprising the steps of;
   a) combining an agent to be tested with a composition comprising said host cell expressing said polypeptide under conditions suitable for binding; and
   b) detecting the formation of a complex between said agent and said polypeptide.

11. The method of claim 10, wherein the binding of the agent to the host cell expressing the polypeptide is detected using an assay for detection of a G-protein-mediated signal transduction.

12. The method of claim 11, wherein the agent identified is an agent that inhibits the activity of the polypeptide, and wherein inhibition of said activity results in increased G-protein-mediated signal transduction.

13. The method of claim 10, wherein said host cell is a hematopoietic cell.

14. The method of claim 13, wherein said hematopoietic cell is a megakaryocyte progenitor cell or a mature megakaryocyte.

15. A method for identifying an agent that binds to a polypeptide encoded by a nucleic acid molecule that hybridizes in 6×sodium chloride/sodium citrate (SSC) at 45° C. followed by one or more washes in 0.2×SSC, 0.1 % SDS at 65° C. to a nucleic acid molecule comprising the nucleotide sequence SEQ ID NO:1, SEQ ID NO:3, nucleotides 160–864 of SEQ ID NO:1, nucleotides 134–838 of SEQ ID NO:3, or the complement thereof, said polypeptide having the ability to activate GTPase, said method comprising the steps of:
   a) combining an agent to be tested with a composition comprising said polypeptide under conditions suitable for binding; and
   b) detecting the formation of a complex between said agent and said polypeptide.

16. The method of claim 15, wherein the binding of the agent to the polypeptide is detected by a method selected from the group consisting of:
   a) directly detecting the binding of the agent to the polypeptide; and
   b) detecting the binding of the agent to the polypeptide using a competition binding assay.

17. A method for identifying an agent that binds to a host cell expressing a polypeptide encoded by a nucleic acid molecule that hybridizes in 6×sodium chloride/sodium citrate (SSC) at 45° C. followed by one or more washes in 0.2×SSC, 0.1% SDS at 65° C. to a nucleic acid molecule comprising the nucleodtide sequence SEQ ID NO:1, SEQ ID NO:3, nucleotides 160–864 of SEQ ID NO:1, nucleotides 134–838 of SEQ ID NO:3, or the complement thereof, said polypeptide having the ability to activate GTPase, said method comprising the steps of:
   a) combining an agent to be tested with a composition comprising said host cell expressing said polypeptide under conditions suitable for binding; and
   b) detecting the formation of a complex between said agent and said polypeptide.

18. The method of claim 17, wherein the binding of the agent to the host cell expressing the polypeptide is detected using an assay for detection of a G-protein-mediated signal transduction.

19. The method of claim 18, wherein the agent identified is an agent that inhibits the activity of the polypeptide, and wherein inhibition of said activity results in increased G-protein-mediated signal transduction.

20. The method of claim 17, wherein said host cell is a hematopoietic cell.

21. The method of claim 20, wherein said hematopoietic cell is a megakaryocyte progenitor cell or a mature megakaryocyte.

22. A method for identifying an agent that binds to a polypeptide encoded by a nucleic acid molecule that hybridizes in 6×sodium chloride/sodium citrate (SSC) at 42° C. followed by washing with 1×SSC at 55° C. to a nucleic acid molecule comprising the nucleotide sequence SEQ ID NO:1, SEQ ID NO:3, nucleotides 160–864 of SEQ ID NO:1, nucleotides 134–838 of SEQ ID NO:3, or the complement thereof, said polypeptide having the ability to activate GTPase, said method comprising the steps of:
   a) combining an agent to be tested with a composition comprising said polypeptide under conditions suitable for binding; and
   b) detecting the formation of a complex between said agent and said polypeptide.

23. The method of claim 22, wherein the binding of the agent to the polypeptide is detected by a method selected from the group consisting of:
   a) directly detecting the binding of the agent to the polypeptide; and
   b) detecting the binding of the agent to the polypeptide using a competition binding assay.

24. A method for identifying an agent that binds to a host cell expressing a polypeptide encoded by a nucleic acid molecule that hybridizes in 6×sodium chloride/sodium citrate (SSC) at 42° C. followed by washing with 1×SSC at 55° C. to a nucleic acid molecule comprising the nucleotide sequence SEQ ID NO: 1, SEQ ID NO:3, nucleotides 160–864 of SEQ ID NO: 1, nucleotides 134–838 of SEQ ID NO:3, or the complement thereof, said polypeptide having the ability to activate GTPase, said method comprising the steps of:
   a) combining an agent to be tested with a composition comprising said host cell expressing said polypeptide under conditions suitable for binding; and
   b) detecting the formation of a complex between said agent and said polypeptide.

25. The method of claim 24, wherein the binding of the agent to the host cell expressing the polypeptide is detected using an assay for detection of a G-protein-mediated signal transduction.

26. The method of claim 25, wherein the agent identified is an agent that inhibits the activity of the polypeptide, and wherein inhibition of said activity results in increased G-protein-mediated signal transduction.

27. The method of claim 24, wherein said host cell is a hematopoietic cell.

28. The method of claim 27, wherein said hematopoietic cell is a megakaryocyte progenitor cell or a mature megakaryocyte.

29. A method for identifying an agent that binds to a polypeptide having the ability to activate GTPase, said polypeptide encoded by a nucleic acid molecule that shares at least 75% identity to the nucleotide sequence depicted in SEQ ID NO:1, SEQ ID NO:3, nucleotides 160–864 of SEQ ID NO:1, nucleotides 134–838 of SEQ ID NO:3, or the complement thereof, said method comprising the steps of:
  a) combining an agent to be tested with a composition comprising said polypeptide under conditions suitable for binding; and
  b) detecting the formation of a complex between said agent and said polypeptide.

30. The method of claim 29, wherein the binding of the agent to the polypeptide is detected by a method selected from the group consisting of:
  a) directly detecting the binding of the agent to the polypeptide; and
  b) detecting the binding of the agent to the polypeptide using a competition binding assay.

31. The method of claim 29, wherein the nucleic acid molecule shares at least 85% identity to the nucleotide sequence depicted in SEQ ID NO: 1, SEQ ID NO:3, nucleotides 160–864 of SEQ ID NO:1, nucleotides 134–838 of SEQ ID NO:3, or the complement thereof.

32. The method of claim 29, wherein the nucleic acid molecule shares at least 95% identity to the nucleotide sequence depicted in SEQ ID NO: 1, SEQ ID NO:3, nucleotides 160–864 of SEQ ID NO:1, nucleotides 134–838 of SEQ ID NO:3, or the complement thereof.

33. A method for identifying an agent that binds to a host cell expressing a polypeptide having the ability to activate GTPase, said polypeptide encoded by a nucleic acid molecule that shares at least 75% identity to the nucleotide sequence depicted in SEQ ID NO:1, SEQ ID NO:3, nucleotides 160–864 of SEQ ID NO: 1, nucleotides 134–838 of SEQ ID NO:3, or the complement thereof, said method comprising the steps of:
  a) combining an agent to be tested with a composition comprising said host cell expressing said polypeptide under conditions suitable for binding; and
  b) detecting the formation of a complex between said agent and said polypeptide.

34. The method of claim 33, wherein the binding of the agent to the host cell expressing the polypeptide is detected using an assay for detection of a G-protein-mediated signal transduction.

35. The method of claim 34, wherein the agent identified is an agent that inhibits the activity of the polypeptide, and wherein inhibition of said activity results in increased G-protein-mediated signal transduction.

36. The method of claim 33, wherein said host cell is a hematopoietic cell.

37. The method of claim 36, wherein said hematopoietic cell is a megakaryocyte progenitor cell or a mature megakaryocyte.

38. The method of claim 33, wherein the nucleic acid molecule shares at least 85% identity to the nucleotide sequence depicted in SEQ ID NO:1, SEQ ID NO:3, nucleotides 160–864 of SEQ ID NO:1, nucleotides 134–838 of SEQ ID NO:3, or the complement thereof.

39. The method of claim 33, wherein the nucleic acid molecule shares at least 95% identity to the nucleotide sequence depicted in SEQ ID NO:1, SEQ ID NO:3, nucleotides 160–864 of SEQ ID NO:1, nucleotides 134–838 of SEQ ID NO:3, or the complement thereof.

40. A method for identifying an agent that binds to a polypeptide having the ability to activate GTPase, said polypeptide having at least 75% identity with a polypeptide selected from the group consisting of:
  a) a polypeptide comprising the amino acid sequence of SEQ ID NO:2 or SEQ ID NO:4;
  b) a polypeptide comprising an amino acid sequence encoded by the cDNA insert of the plasmid deposited with ATCC as Accession Number 207048; or
  c) a polypeptide comprising an amino acid sequence encoded by the DNA sequence obtained from overlapping clones deposited with ATCC as Accession Numbers 207049 and 207050, said method comprising the steps of;
  a) combining an agent to be tested with a composition comprising said polypeptide under conditions suitable for binding; and
  b) detecting the formation of a complex between said agent and said polypeptide.

41. The method of claim 40, wherein the binding of the agent to the polypeptide is detected by a method selected from the group consisting of:
  a) directly detecting the binding of the agent to the polypeptide; and
  b) detecting the binding of the agent to the polypeptide using a competition binding assay.

42. The method of claim 40, wherein the polypeptide has at least 85% identity with a polypeptide selected from the group consisting of:
  a) a polypeptide comprising the amino acid sequence of SEQ ID NO:2 or SEQ ID NO:4;
  b) a polypeptide comprising an amino acid sequence encoded by the cDNA insert of the plasmid deposited with ATCC as Accession Number 207048; or
  c) a polypeptide comprising an amino acid sequence encoded by the DNA sequence obtained from overlapping clones deposited with ATCC as Accession Numbers 207049 and 207050.

43. The method of claim 40, wherein the polypeptide has at least 95% identity with a polypeptide selected from the group consisting of:
  a) a polypeptide comprising the amino acid sequence of SEQ ID NO: 2 or SEQ ID NO: 4;
  b) a polypeptide comprising an amino acid sequence encoded by the cDNA insert of the plasmid deposited with ATCC as Accession Number 207048; or
  c) a polypeptide comprising an amino acid sequence encoded by the DNA sequence obtained from overlapping clones deposited with ATCC as Accession Numbers 207049 and 207050.

44. A method for identifying an agent that binds to a host cell expressing a polypeptide having the ability to activate GTPase, said polypeptide having at least 75% identity with a polypeptide selected from the group consisting of:
  a) a polypeptide comprising the amino acid sequence of SEQ ID NO:2 or SEQ ID NO:4;
  b) a polypeptide comprising an amino acid sequence encoded by the cDNA insert of the plasmid deposited with ATCC as Accession Number 207048; or
  c) a polypeptide comprising an amino acid sequence encoded by the DNA sequence obtained from overlapping clones deposited with ATCC as Accession Numbers 207049 and 207050, said method comprising the steps of;
  a) combining an agent to be tested with a composition comprising said host cell expressing said polypeptide under conditions suitable for binding; and b) detecting the formation of a complex between said agent and said polypeptide.

45. The method of claim 44, wherein the binding of the agent to the host cell expressing the polypeptide is detected using an assay for detection of a G-protein-mediated signal transduction.

46. The method of claim 45, wherein the agent identified is an agent that inhibits the activity of the polypeptide, and wherein inhibition of said activity results in increased G-protein-mediated signal transduction.

47. The method of claim 44, wherein said host cell is a hematopoietic cell.

48. The method of claim 47, wherein said hematopoietic cell is a megakaryocyte progenitor cell or a mature megakaryocyte.

49. The method of claim 44, wherein the polypeptide has at least 85% identity with a polypeptide selected from the group consisting of:

a) a polypeptide comprising the amino acid sequence of SEQ ID NO:2 or SEQ ID NO:4;

b) a polypeptide comprising an amino acid sequence encoded by the cDNA insert of the plasmid deposited with ATCC as Accession Number 207048; or c) a polypeptide comprising an amino acid sequence encoded by the DNA sequence obtained from overlapping clones deposited with ATCC as Accession Numbers 207049 and 207050.

50. The method of claim 44, wherein the polypeptide has at least 95% identity with a polypeptide selected from the group consisting of:

a) a polypeptide comprising the amino acid sequence of SEQ ID NO:2 or SEQ ID NO:4;

b) a polypeptide comprising an amino acid sequence encoded by the cDNA insert of the plasmid deposited with ATCC as Accession Number 207048; or c) a polypeptide comprising an amino acid sequence encoded by the DNA sequence obtained from overlapping clones deposited with ATCC as Accession Numbers 207049 and 207050.

* * * * *